US006835724B2

(12) United States Patent
Stache et al.

(10) Patent No.: US 6,835,724 B2
(45) Date of Patent: Dec. 28, 2004

(54) CORTICOID 17,21-DICARBOXYLIC ESTERS AND CORTICOSTEROID 17-CARBOXYLIC ESTER 21-CARBONIC ESTERS, PROCESSES FOR THEIR PREPARATION AND PHARMACEUTICALS CONTAINING THESE COMPOUNDS

(75) Inventors: Ulrich Stache, Hofheim (DE); Hans-Georg Alpermann, Königstein (DE); Walter Dürckheimer, Hattersheim (DE); Manfred Bohn, Hofheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 513 days.

(21) Appl. No.: 08/897,455

(22) Filed: Jul. 22, 1997

(65) Prior Publication Data

US 2002/0103392 A1 Aug. 1, 2002

Related U.S. Application Data

(63) Continuation of application No. 08/590,624, filed on Jan. 24, 1996, now abandoned, which is a continuation of application No. 08/310,791, filed on Sep. 29, 1994, now abandoned.

(30) Foreign Application Priority Data

Oct. 5, 1993 (DE) ........................ P 43 33 920

(51) Int. Cl.[7] .............................. A61K 31/56; C07J 5/00
(52) U.S. Cl. ........................ 514/179; 514/180; 514/181; 552/574; 552/576
(58) Field of Search .................. 552/569, 570, 552/572, 573, 574, 575, 576, 577, 578, 593, 594, 595; 540/108, 110, 111, 114, 115, 116, 120; 514/169, 172, 174, 175, 176, 178, 179, 180, 181

(56) References Cited

U.S. PATENT DOCUMENTS 3,133,940 A * 5/1964 Oughton et al. ....... 260/397.45
3,201,391 A * 8/1965 Bowers ................. 260/239.55

(List continued on next page.)

FOREIGN PATENT DOCUMENTS

| DE | 2 204 366 | 8/1973 |
|---|---|---|
| DE | 25-34-051 | 2/1976 |
| EP | 0 072 200 | 2/1983 |
| EP | A-095-894 | 12/1983 |
| EP | 0 156 643 | 10/1985 |
| EP | B-170500 | 2/1986 |
| EP | A470617 A2 | 2/1992 |
| ES | 538692 | 12/1984 |
| GB | 1-516-095 | 6/1978 |
| JP | 53059655 | 5/1978 |

OTHER PUBLICATIONS

Derwent Abstract of DE 2 204 366.
Sugai et al., "Studies on Topical Antiinflammatory Corticosteroids. I. Syntheses and Vasoconstrictive Activies of 11β,17α,21–Trihydroxy–6α–methyl–1,4–pregnadiene–3, 20–dione 17–Ester and 17,21–Diester Derivatives", Chem. Pharm. Bull. 33(5):1889–1898 (1995).

(List continued on next page.)

Primary Examiner—Barbara P. Badio
(74) Attorney, Agent, or Firm—Finnegan, Henderson, Farabow, Garrett & Dunner, L.L.P.

(57) ABSTRACT

Corticoid 17,21-dicarboxylic esters and corticosteroid 17-carboxylic ester 21-carbonic esters, processes for their preparation and pharmaceuticals containing these compounds Corticoid 17,21-dicarboxylic esters and corticoid 17-carboxylic ester 21-carbonic esters of the formula I:

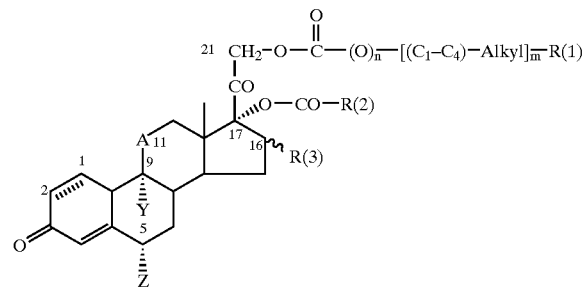

are described, in which A is CHOH and CHCl, $CH_2$, C=O or 9(11) double bond; Y is H, F or Cl; Z is H, F or methyl; R(1) is aryl or hetaryl; R(2) is alkyl and R(3) is H or methyl. They are obtained, inter alia, by reacting a compound of the formula II:

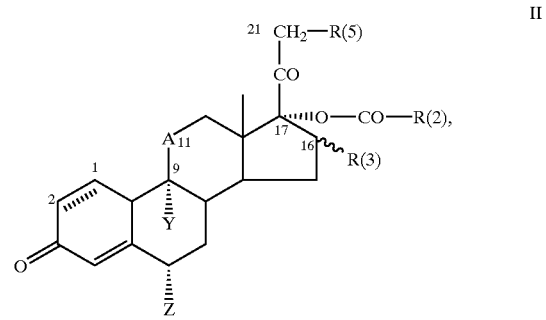

in which R(5) is OH, with an activated carboxylic acid of the formula III:

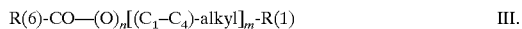

They have a very strong local and topical antiinflammatory action and exhibit a very good ratio of local to systemic antiinflammatory effects. They are used, inter alia, as agents for treating inflammatory dermatoses.

12 Claims, No Drawings

U.S. PATENT DOCUMENTS

| | | | | |
|---|---|---|---|---|
| 3,201,429 A | * | 8/1965 | Djerassi et al. | 260/397.47 |
| 4,176,126 A | | 11/1979 | Annen et al. | |
| 4,242,334 A | | 12/1980 | Stache et al. | |
| 4,377,575 A | | 3/1983 | Stache et al. | 424/243 |
| 4,555,507 A | * | 11/1985 | Annen et al. | 514/172 |
| 4,567,172 A | * | 1/1986 | Kamano et al. | 514/179 |
| 4,619,922 A | * | 10/1986 | Annen et al. | 514/180 |
| 4,645,763 A | * | 2/1987 | Annen et al. | 514/178 |
| 4,655,971 A | * | 4/1987 | Page et al. | 260/397.45 |
| 4,701,451 A | * | 10/1987 | Annen et al. | 514/180 |
| 4,918,065 A | * | 4/1990 | Stindl et al. | 514/179 |
| 5,026,693 A | * | 6/1991 | Villax et al. | 514/180 |

OTHER PUBLICATIONS

Sota et al., "Synthesis and Antiinflammatory Activity of Hydrocortisone 12,21–Diesters", Yakugaku Zasshi, 102(4):365–370 (1982).

English Derwent Abstract of DE 25–34–051, 1976.

English Derwent Abstract of ES 538.692, 1984.

Isogai et al., "Binding Affinities Of Mometasone Furoate And Related Compounds Including Its Metabolites For The Glucocorticoid Receptor Of Rate Skin Tissue," *The Journal Of Steroid Biochemistry And Molecular Biology*, vol. 44, No. 2, Feb. 1993.

Arrieta et al., Reagents and Synthetic Methods 28. Modified Procedures for Anhydrization, Esterification and Thiolesterification of Carboxylic Acids by Means of Available Phosphorus Reagents, Synth. Commun. 13 (6) :471–87 (1983).

Ballester–Rodes et al., N,N–Bis (2–Oxo–3–Oxazolidinyl) Phosphordiamidic Chloride (CLSPO) : A New Strategy for the Ester Function Preparation, Synth. Commun. 14 (6) :515–20 (1984).

Staab et al., Synthese von Carbonsaureestern nach der Imidazolidmethode, Prednicarbate, Merck Index 11:7717, p. 1223 (1989).

Tonelli et al., A Bio–assay for the Concomitant Assessment of the Anti–phlogistic and Thymolytic Activities of Topically Applied Corticoids, Endocrinology 77:625–34 (1965).

Winter et al., Conversion of 6,7–$h^3$–Estradiol–17β into Estrone and Estradiol–17α in the Mature Mail Dog, Proc. Soc. Exp. Biol. (New York) 111 (3) :544–47 (1962).

* cited by examiner

CORTICOID 17,21-DICARBOXYLIC ESTERS AND CORTICOSTEROID 17-CARBOXYLIC ESTER 21-CARBONIC ESTERS, PROCESSES FOR THEIR PREPARATION AND PHARMACEUTICALS CONTAINING THESE COMPOUNDS

This application is a continuation of application Ser. No. 08/590,624, filed Jan. 24, 1996, now abandoned; which is a continuation of application Ser. No. 08/310,791, filed Sep. 29, 1994, abandoned.

The invention relates to corticoid 17,21-dicarboxylic esters and corticoid 17-carboxylic ester 21-carbonic esters of the formula I:

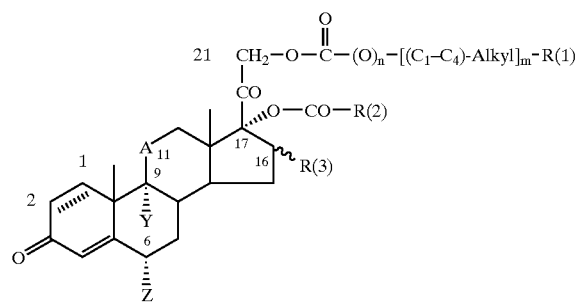

in which:

A is CHOH and CHCl in arbitrary steric arrangement, $CH_2$, C=O or 9(11) double bond, Y is hydrogen, fluorine or chlorine, Z is hydrogen, fluorine or methyl, R(1) is optionally substituted or fused aryl or hetaryl $(C_1-C_4)$-alkyl is saturated, unsaturated once or more than once, branched by further alkyl groups, unsubstituted or inserted or substituted by heteroatoms O, S or N, n is zero or 1, m is zero or 1, R(2) is linear or branched $(C_1-C_8)$-alkyl

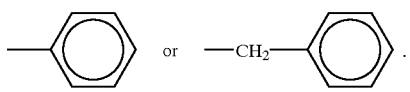

R(3) is hydrogen or α- or β-methyl.

Corticoid 17,21-dicarboxylic esters and corticoid 17-carboxylic ester 21-carbonic esters of the formula I are preferred in which:

R(1), A, Y, Z and R(3) are defined as above,

R(2) is linear or branched $(C_1-C_8)$-alkyl

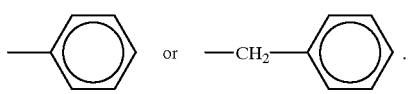

The invention also relates to a process for preparing a compound I, in which process a) a compound of the formula II:

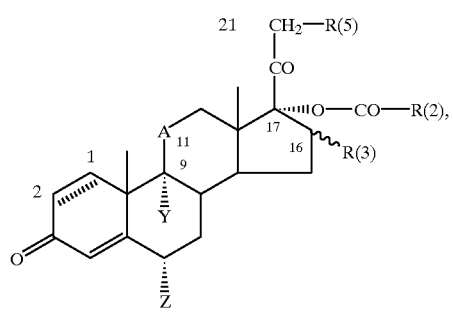

in which R(5) is OH and the remaining substituents have the abovementioned meanings, a1) is reacted with an activated carboxylic acid of the formula III, preferably a halide or anhydride or azolide,

in which:

n is zero, m is zero or 1, and $[(C_1-C_4)$-alkyl] and R(1) have the abovementioned meanings, and R(6) is Cl, Br, $O[-CO-(O)_n-](C_1-C_4)$-alkyl$]_m$-R(1)$_1$, $-O-C(O)CF_3$, or another activated acid radical, or a2) is reacted with a haloformate of the formula III, in which n is 1, m is zero or 1, $[(C_1-C_4)$-alkyl] and R(1) have the abovementioned meanings and R(6) is Cl, Br or I, or a3) is reacted with a carboxylic acid of the formula III itself, in which R(6) is OH, and n is zero, and the other substituents are given in formula III, in the presence of water-eliminating reagents (DCCI, etc.), or in which b) compounds of the formula II:

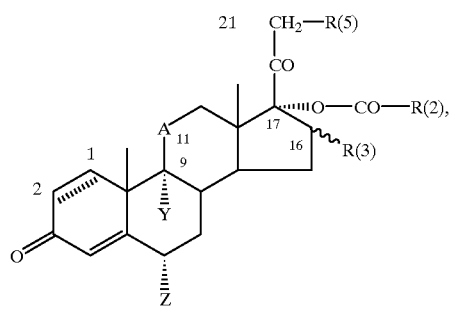

in which R(5) is Br, I, or a sulfonic aryl ester group or sulfonic alkyl ester group, and the other substituents have the meaning given in formula I, are reacted with a salt, preferably a K or Na salt or a trialkylammonium salt, of a carboxylic acid of the formula III:

in which

R(6) is $-[O^-Me^+]$, and n is zero, and the other substituents have the meanings given in formula III, Me preferably being the cation of an alkali metal salt or of a trialkylammonium salt.

The steroid 17-carboxylic esters with a free 21-hydroxyl group of the formula II [R(5)=OH], which are required as starting substances, are as a rule known or are prepared by known methods.

The stippled line between carbon atoms 1 and 2 indicates that this bond can be a single bond or an unsaturated bond.

The steroid 17-carboxylic esters with R(5) being Br, I, —OSO$_2$-aryl or —OSO$_2$-alkyl in formula II are known as a rule or are prepared by known methods, e.g. in analogy with corresponding corticoid 17-alkyl carbonate 21-compounds in accordance with U.S. Pat. No. 4,377,575 (HOE 78/F 082) and EP-A-470 617 (HOE 90/F 241). The 17-carboxylic esters of the following corticosteroids come into consideration in this context:

prednisolone, prednisone, 6α-methylprednisolone, 6α,61α-dimethylprednisolone, 16α-methylprednisolone, hydrocortisone (cortisol), cortisone, 6α-methylcortisol, Reichstein's substance S, 11-desoxy-9(11)-dehydroprednisolone, 6α-fluoroprednisolone, dexamethasone, 6α-fluorodexamethasone, 9α-fluoroprednisolone, 6α,9α-difluoroprednisolone, 6α-methyl-9α-fluoroprednisolone, betamethasone and clobetasol.

The carboxylic acids of the formula III [R(6) is OH and n is zero] which are used as reaction partners, and their activated derivatives, such as the halides [R(6)=Cl, Br or I, or their anhydrides], or their azolides [R(6) is imidazolide or triazolide], or their salts [R(6) is (MeO)—, preferably (KO)— or (NaO)—], are as a rule known and are prepared, where appropriate, by general preparative methods. Examples of carboxylic acids according to formula III [R(6) is OH and n is zero] which can be used in accordance with the invention are to be found in the list at the end of the text prior to the claims.

All carboxylic acids coming into this category carry, in their acid radical, an aryl or hetaryl group which is optionally substituted by methylenedioxy, halogen, alkyl, alkoxyl, acyl, thioalkyl, thioacyl, nitro, amino, aminoalkyl, amido, cyano, oxyacyl, oxyaryl, etc., or is optionally fused. The aryl and hetaryl groups are essential constituents of the invention.

As is demonstrated in the pharmacological section, corticoid 17,21-dicarboxylic esters of this type (=21-aryl ester or 21-hetaryl ester type), in particular, often exhibit qualities of effect which are clearly superior, as regards the local/systemic ratio of antiinflammatory effect, to those of structurally related corticoid 17,21-dicarboyxlic esters or structurally related corticoid 17-alkyl carbonate 21-carboxylic esters which do not carry any aryl or hetaryl group in the 21-acid residue.

Detailed description of the conduct of the individual reactions in the processes for preparing the products according to Formula I according to the invention:

Regarding process variant a:

In order to prepare 21-carboxylic esters of the abovementioned type, either carbonyl halides or carboxylic azolides of the formula IV $$R(6)\text{-OC—}[(C_1-C_4\text{-alkyl})]_m\text{-R(1)} \qquad IV,$$

in which:

R(6) is Cl, Br, I,

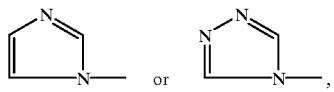

m is zero or 1, and
R(1) and (C$_1$–C$_4$)-alkyl have the meanings given for formula III,
or carboxylic anhydrides of the formula V:

$$O\{\text{—OC—}[(C_1-C_4)\text{-alkyl}]_m\text{-R(1)}\}_2 \qquad V,$$

in which
m is zero or 1, and
R(1) and (C$_1$–C$_4$)-alkyl have the meanings given for formula III, are preferably used. In both cases, the carboxylic acids on which they are based, and which are given in the list, can be used, preferably their carbonyl chlorides, carboxylic anhydrides, carboxylic imidazolides and carboxylic triazolides.

R(6) in formula IV can also comprise other groups which activate the carboxyl group in carboxylic acids for esterification, such as, for example, —O—CO—CF$_3$, or the activated carboxylic acids which can be prepared from phosphonic or phosphinic anhydrides (e.g. propylphosphonic anhydride) or polyphosphoric anhydride (PPA).

Additional phosphorus reagents which can bring about mild esterification of organic carboxylic acids with the 21-alcohol group of corticoid 17-alkyl carbonates are cited or described in the literature references Synth. Commun. 13, 471 ff (1983) and Synth. Commun. 14, 515 ff (1984).

In order to carry out the esterification using a carbonyl halide or carboxylic anhydride or a haloformate, the steroid component is dissolved in an inert solvent, for example in an ether, such as dioxane, tetrahydrofuran or diglyme, or in optionally halogenated hydrocarbons, such as benzene, toluene, cyclohexane, methylene chloride or chloroform, or in acetone, or in a mixture of these solvents. In order to remove the hydrohalic acid which is produced in the reaction, 1 to 1000 molar equivalents of a tertiary base, such as pyridine, quinoline, triethylamine, dimethylaniline, dimethylaminopyridine, etc., are added. However, an inorganic base, such as sodium hydrogen carbonate or calcium carbonate, can also be used for removing the acid. 1 to 200 molar equivalents, preferably 1–3 molar equivalents, of one of the above-listed acylating agents, optionally dissolved in one of the above-listed solvents, are then added dropwise at a temperature of −40° C. up to the boiling point of the solvent used, preferably at a temperature of 0° C. to 25° C. Subsequently, the reaction mixture is left to stand for one to 120 hours at a temperature of −40° C. up to the boiling point of the solvent, preferably at a temperature of 0° C. to 25° C.

When using carboxylic anhydrides as acylating agents, it is now and then advantageous not to add solvents. As a rule, it is sufficient simply to add the organic base preferably pyridine, to the acid anhydride, which may optionally be used in excess.

Particularly in the case of sensitive (and sometimes unstable) carboxylic acid derivatives of the abovementioned type, in particular when using phenylacetyl chlorides or anhydrides and hetarylacetyl chlorides and anhydrides, it is of great preparative advantage, and of great advantage with regard to the selectivity of the reaction, if the corticoid 17-carboxylic esters having a free 21-hydroxyl group are reacted with 1 to 4 molar equivalents of the chloride or anhydride at −10° to +6° C. (maximum 20° C.) in chlorinated hydrocarbons, such as, preferably, dichloromethane, and with 1 to 4 molar equivalents of a pyridine base, preferably dimethylaminopyridine. Under these circumstances, the reaction products of the formula I are obtained in high purity, with negligible quantities of byproducts, in particular 11-acylated products (monitoring of the course of the reactions with TLC), that is the reactions are highly regioselective with regard to conversion of the 21-hydroxyl group.

In the case of the reactions with carbonyl chlorides, absolute dioxane or tetrahydrofuran is frequently advantageously added to the reaction mixture, e.g. in the case of benzoyl chloride, where, e.g., the ratio of dioxane/pyridine is approximately 1:1; in addition, in order to accelerate the reaction, the reaction mixture is often, particularly in the case of sterically hindered or less reactive carbonyl chlorides or carboxylic anhydrides, heated to about 60° C. (monitoring of the course of the reaction with TLC).

The reaction products can be characterized using thin layer chromatography (TLC); in this context, the reaction products have $R_F$ values of about 0.65 to 0.8. As a rule, the reaction products are characterized by mass spectra using MS=m/z= . . . (M+H$^+$) (FAB spectra, as a rule); the monoisotopic molar masses are registered in each case. The M+H$^+$ values were rounded up in each case. IR spectra, $^1$H-NMR spectra and UV spectra can also be enlisted for the characterization.

For the working up, the reaction mixture is poured into water, to which sodium chloride and sodium bicarbonate may, where appropriate, have been added, in association with which the reaction products generally precipitate out in crystalline form, frequently only after standing for some length of time. Oily or waxy reaction products are concentrated by extracting, while shaking, with a suitable extracting agent, and then evaporating. If necessary, the reaction products can be fractionated or purified by recrystallization or by chromatography. Intensive digestion in an organic solvent which either does not dissolve the reaction product or else dissolves it as little as possible, for example diethyl ether or cyclohexane, or a mixture of these components, may also frequently suffice for the further purification of the reaction products.

When using carboxylic azolides, the esterification is expediently carried out as a one-pot reaction. In this case, arylacetic acid or hetarylacetic acid, for example, or another carboxylic acid of the formula III [R(6) is OH, n is zero], is dissolved in absolute pyridine, and a preferably equimolar quantity of N,N-carbonyldiimidazole or N,N-carbonyl[1H-1,2,4-triazole] is added, with the corresponding acid azolides forming at 0° to 20°. After adding an approximately equimolar quantity of corticoid 17-carboxylic ester of the formula II [R(5)=OH] and a catalytic quantity of a base, preferably sodium hydride or sodium imidazolide, the mixture is stirred in pyridine at between 0° and 40° C., preferably 20°, and then worked up in the customary manner.

However, the carboxylic azolide, which has previously been prepared in absolute tetrahydrofuran with equimolar quantities of N,N'-carbonylazolide and carboxylic acid, and then isolated, can also be added to the steroid dissolved, in solvents such as pyridine, dimethylformamide or tetrahydrofuran, with the subsequent procedure being as described above [see also Chem. Ber. 95, pp. 1284 ff. (1962)].

When esterifying with the aid of phosphonic or phosphinic anhydrides, equimolar quantities of carboxylic acid and corticoid 21-alcohol in absolute pyridine are preferably added to 50% strength propanephosphoric anhydride in methylene chloride at 20° to 60° C., while also adding 4-dimethylaminopyridine as an acid-capturing agent, with the working up being carried out as usual (pouring into ice water, extracting with ethyl acetate, washing with 5% $KHSO_4$, distilling off and crystallizing). Polyphosphoric anhydride (PPA) may also be employed instead of phosphonic anhydrides.

An additional advantageous esterification process, which is applicable to the carboxylic acids according to formula III [R(6) is OH and n is zero] or included in the list, is the direct reaction of corticoid 17-carboxylic esters of the formula II [R(5) is OH] using water-removing agents such as carbodiimides, preferably N,N'-dicyclohexylcarbodiimide (DCCI). In some cases, "molecular sieves" can also be used as water-removing agents in place of DCCI.

The esterification can be catalytically accelerated or optimized by adding an acid, e.g. sulfuric acid, phosphoric acid, hydrochloric acid, diphenylphosphoric acid or p-toluene sulfonic acid, or their pyridinium salts, or an organic base, for example, dimethylaminopyridine (=particularly advantageous in halogenated solvents, for example, methylene chloride, or in dimethylformamide), something which is very advantageous, particularly in the case of carboxylic acids, e.g. of the indolylacetic acid, pyrrolecarboxylic acid, arylacetic acid and hetarylacetic acid types, etc., which are either sensitive or otherwise only react with difficulty. In this context, it is surprising that the secondary 11-hydroxyl group in the corticoid 17-carboxylic esters which are employed is not (practically) as a rule esterified simultaneously, as is occasionally observed when esterifying with the corresponding acid halides.

In a particular variant of the process, a catalytic quantity of the pyridinium salt of sulfuric acid is added to a solution of one molar equivalent of corticoid 17-carboxylic ester 21-alcohol [formula II, R(5) is OH] and 1 to 4 molar equivalents, preferably 2 equivalents, of carboxylic acid of the formula III [R(6) is OH and n is zero] in absolute pyridine, and this is followed, after about 20 min., by the addition of 1 to 4 molar equivalents, preferably 1 to 2 molar equivalents, of dicyclohexylcarbodiimide. The mixture is then stirred at 0° to 50° C., preferably 20° C., until a sample examined by TLC indicates that the starting carboxylic acid has disappeared and that only desired carboxylic acid 21-corticoid esters of the formula I are present. The dicyclohexylurea which has formed is filtered off and the filtrate is then expediently poured into water; this is then followed by filtration (in the case of crystal formation) or decantation (in the case of oily or waxy precipitates), washing with water (where appropriate, extraction can also take place with extracting agents, in particular dichloromethane), drying, and recrystallization as usual; alternatively, if required, the reaction products are purified by customary chromatography, preferably on silica gel.

Instead of pyridine, other inert solvents, such as, for example, tetrahydrofuran, dioxane, methylene chloride or dimethylformamide, expediently with the addition of tertiary bases, for example pyridine or 4-dimethylaminopyridine, can also be used in some cases. The latter solvents are to be preferred when molecular sieves are used as water-removing agents.

In addition to this, the following variant has proved valuable for esterifying with the sensitive arylacetic acids and heterylacetic acids: 1 equivalent of carboxylic acid is dissolved at 0° C. in absolute dichloromethane, and 1 equivalent of DCCI, up to 0.2 equivalent of 4-N,N'-dimethylaminopyridine and a solution of 1 equivalent of corticosteroid 17-carboxylic ester 21-alcohol in absolute dichloromethane are then added in succession and the mixture is stirred at 20° C. for 18 to 48 hours. After the customary working up, the desired ester of the formula I can be obtained in pure form. A molecular sieve can also be used instead of DCCI.

In a further esterification method, 1 molar equivalent of carboxylic acid and trifluroacetic anhydride are added to corticoid 17-carboxylic ester 21-[tert-butyldimethylsilyl-(O)-ether] in absolute tetrahydrofuran, and the customary working up takes place after stirring at 20° C. for about 1 to 6 hours.

However, the carboxylic acid and the corticoid 17-carboxylic ester 21-alcohol (free form) can also be reacted directly with trifluoroacetic anhydride to give the desired 21-carboxylic ester (=formation of the mixed anhydride from carboxylic acid and trifluoroacetic acid, which anhydride then reacts with the 21-alcohol to give the 21-ester).

Regarding process variant b:

A further advantageous process variant, which leads to the corticoids according to the invention, comprises heating a corticoid 17-carboxylic ester 21-halide, preferably 21-iodide or 21-bromide, or 21-sulfonate, preferably 21-p-chlorobenzene sulfonic ester or 21-methane sulfonic ester, with the metal salts, preferably alkali metal salts or trialkylammonium salts, of the carboxylic acids included in list 2, in inert organic solvents, preferably dimethyl sulfoxide, dimethylformamide, 2-butanone, acetone or acetonitrile, at 20° C. up to the boiling points of the solvents used, preferably at about 50° C., for 1 to 16 hours, preferably 1 to 10 hours, and isolating after the customary working up, preferably pouring in water, filtering or decanting off the precipitate, and customary purification.

In connection with this nucleophilic reaction in which a 21-halide or 21-sulfonic ester group is exchanged for a carboxylic ester group, it is surprising that, under the preferably alkaline reaction conditions, the 17-carboxylic ester group, which is jointly responsible for the activity profile, is not simultaneously saponified in the process products.

The compounds I prepared according to procedures a) and b) are such that a hydroxyl group in the 11 position can, where appropriate, be oxidized to the keto group by customary methods. This oxidation is preferably carried out using chromium trioxide in an acid medium and in an inert organic solvent. A 9(11) double bond which is present in the corticoid moiety can, where appropriate, be converted by adding hydrohalic acid or by chlorine, in accordance with the usual known methods, into the corresponding corticoid 17,21-dicarboxylic esters according to the invention having a 11β-hydroxyl, 9α-halide group (9αF,Cl) or 11β,9α-dichloro group.

The process products possess valuable pharmacological properties. They have, in particular, a very strong local and topical antiinflammatory action, and some of them exhibit, surprisingly, a very good ratio of local to systemic antiinflammatory effect, which ratio is often markedly superior, as can be deduced from pharmacological standard tests to that of analogous corticoid 17,21-diesters, and, for example to that of known corticoid 17-alkyl carbonate 21-esters, which do not carry any aryl or hetaryl group in the 21-ester radical, such as, for example, 21-ester groups having a 21-alkyl group. Accordingly, an agent for treating inflammatory dermatoses and comprising a compound of the formula I is also a subject of the invention.

The process products can be used in veterinary and human therapy in the form of suspensions, ointments, creams, sprays, etc., for treating inflammatory dermatoses of a wide variety of origins. In this context, it is to be emphasized as being particularly advantageous for the local and topical forms of therapy that, owing to their extremely favorable ratio of local to systemic antiinflammatory effect, even in the case of lengthy therapy at high dosage rates, the process products are able in practice only to elicit trivial systemic side effects. In the case of external treatment, ointments, creams, suspensions, etc. are used at a concentration of 0.01 to 2% by weight. In particular, the process products exhibit a split (ratio) of local/systemic antiinflammatory effects in pharmacological tests which is sometimes appreciably better than that of corresponding preparations having a 21-ester group lacking aryl or hetaryl moieties, as are found in the compounds according to the invention, in the ester moiety. In addition, some of the process products also exhibit a more powerful local antiinflammatory action than do the abovementioned analog preparations. In addition to this, the corticoid 17,21-dicarboyxlic esters according to the invention can often have a still lower atrophoderma-generating effect than do the abovementioned analogous corticoid 17,21-diesters, which is a further advantage for their use in dermatotherapeutic treatment.

Corticoid 17-carboxylic ester 21-cinnamic esters, in particular those substituted in the 4-position in the aromatic moiety by methoxy, methylenedioxy or ethoxy, can, by way of their antiinflammatory effect, possess an additional sunscreen effect against solar radiation, in particular UV-B and UV-A radiation. The same also applies to corticoid 17-carboxylic acid 21-esters which have a N,N-dialkyl benzoate, preferably a 4-(dimethylamino)-benzoate, in the 21-position. These compounds, too, can possess an additional sunscreen effect. Furthermore, corticoid 17-carboxylic esters having a chlorambucil moiety in the 21-ester, as, for example, prednisolone 17-n-butyrate 21-chlorambucil ester, can have antitumorigenic effects which correspond to the effects of the known prednimustine (Merck Index 11, 7718).

In addition to this, the process products according to the invention can be combined in pharmaceutical formulations with diverse antibiotics which are locally active and which are well tolerated by the skin, e.g. of the gentamycin, neomycin, erythromycin or tetracycline type, or of the fusidic acid type, and others. Such combinations of the process products and the locally active antibiotics can be used for treating primary bacterial, or bacterially superinfected, inflammatory dermatoses.

Pharmacological Experimental Section

Thus, prednisolone 17-benzoate 21-phenylacetic ester (I) or betamethasone 17-benzoate 21-phenylacetic ester (II), for example, exhibited a strong local antiinflammatory effect in association with a strikingly favorable split to weak systemic activity, as is evident from the pharmacological test results recorded below [preparation for comparison, prednicarbate (=prednisolone 17-ethyl carbonate 21-propionate (U.S. Pat. No. 4,242,334) and (Merck Index 11, 7717))]:

1. Local antiinflammatory effect in rat croton oil ear edema following epicutaneous application We used the rat ear method of Tonelli et al., Endocrinology, 77, 625 (1965): male Wistar rats from our own colony and weighing about 50 g were treated epicutaneously on the right ear with the irritant or with irritant containing test substance. The left ear remained untreated. TPA (12-o-tetradecanoylphorbol 13-acetate, SIGMA P 8139) dissolved in acetone, 0.2 mg/ml, (of which 20 μl each on the inside and outside) was used for eliciting the inflammation. The corticoids under examination were dissolved in this solution in the given final concentrations. Controls only received the TPA/solvent mixture. The animals were sacrificed using $CO_2$ 4 h after the epicutaneous treatment. Disks measuring 8 mm in diameter were punched out of the right (treated) and the left (untreated) ears and weighed immediately.

This difference, as the parameter for the degree of inflammation, was set at 100 in the controls (mg, x±s). The antiinflammatory effect is characterized by giving the dose in mg/ml which is required for approximately 50% inhibition:

| Treatment | mg/ml | x ± s (mg) | Inhibition in % |
|---|---|---|---|
| Control | — | 21.2 ± 5.1 | — |
| Compound I | 0.1 | 5.0 ± 3.1 | 76 |
| | 0.3 | 3.1 ± 2.5 | 85 |
| | 1.0 | 2.0 ± 1.4 | 91 |
| Compound II | 0.1 | 7.0 ± 3.3 | 67 |
| | 0.3 | 4.9 ± 3.3 | 77 |
| | 1.0 | 1.1 ± 0.9 | 95 |
| Prednicarbate | 0.1 | 5.2 ± 3.3 | 75 |
| | 0.3 | 2.6 ± 2.4 | 88 |

Result: The extrapolated dose which is required for 50% inhibition is 0.03 mg/ml for compound I, compound II and the comparison preparation.

2 a) Examining for systemic antiinflammatory effect in the "antiinflammatory effect following subcutaneous administration: Carrageenan paw edema in rats" test.

The carrageenan paw edema test in rats in accordance with the method described by Winter et al., Proc. Soc. exp. Biol. (New York) 111, 544 (1962) was chosen as the test for the acute systemic antiinflammatory effect. Male Sprague-Dawley rats of about 120 g in weight were given the substances to be tested s.c. (0.2 ml/100 g) dissolved in sesame oil. 30 min later, 0.1 ml of a 0.5% carrageenan solution was injected into the left hind paw. 6 hours later, the degree of swelling was measured volumetrically. Controls were only given sesame oil.

The paw volumes are given in ml, x±s. In this case too, the antiinflammatory effect is characterized by giving the dose in mg/kg required for approximately 50% inhibition.

| Treatment | Dose in mg/kg S.C. | Starting value (ml) | Increase in volume (ml) |
|---|---|---|---|
| Control | — | 1.39 ± 0.09 | 0.58 ± 0.16 |
| Compound I | 0.3 | 1.40 ± 0.12 | 0.46 ± 0.19 |
| | 3.0 | 1.34 ± 0.06 | 0.38 ± 0.15 |
| Compound II | 0.3 | 1.42 ± 0.05 | 0.56 ± 0.09 |
| | 3.0 | 1.31 ± 0.09 | 0.45 ± 0.14 |
| Prednicarbate | 0.3 | 1.44 ± 0.08 | 0.36 ± 0.13 |
| | 3.0 | 1.37 ± 0.07 | 0.09 ± 0.08* |

Result: Evaluation of the experiment using the Dunnett test showed that neither of the dosages of compounds I and II had any significant inhibitory effect, whereas, at 3 mg/kg, prednicarbate had a significant systemic effect (*). Thus, compounds I and II are about 10 times less active than prednicarbate, that is they are to be categorized as being superior to this standard by this factor.

2 b) Examining for systemic effect: gluconeogenesis in rats

A sensitive method for detecting systemic effects on carbohydrate metabolism is to examine the gluconeogenic effect of corticosteroids in the adrenalectomized rat.

Three days prior to the experiment, groups of in each case 6 rats are adrenalectomized under pentobarbital anesthesia and provided with 0.9% sodium chloride solution as drinking fluid. Two days later, i.e. 24 hours before initiating the experiment, the feed is removed in order to reduce the glycogen stores in the liver.

On the day of the experiment, the preparations under examination are administered subcutaneously, dissolved in sesame oil (2 ml/kg). Six hours later, the animals are decapitated, and in each case the liver is removed and 1 g thereof is taken up in 5 ml of 0.6 molar perchloric acid. After homogenization, the free glucose is measured in the supernatant from the centrifugation, while the centrifugation sediment (centrifugate; glycogen) is cleaved enzymically with amyloglucosidase, after which the glucose content is also measured in this fraction (Hexokinase method, Boehringer Mannheim). The following results were obtained (average value±standard deviation):

| Treatment | Dose (mg/kg s.c.) | Liver glycogen | Glycogen + glucose mg/100 g of liver |
|---|---|---|---|
| Control | — | 1.1 ± 0.6 | 11.2 ± 1.7 |
| Compound I | 0.3 | 2.2 ± 2.1 | 20.4 ± 11.7 n.s. |
| | 3.0 | 43.2 ± 25.8 | 96.0 ± 26.2 |
| Compound II | 0.3 | 1.1 ± 0.5 | 10.8 ± 1.3 n.s. |
| | 3.0 | 36.1 ± 45.2 | 81.2 ± 61.7 |
| Prednicarbate | 0.3 | 41.2 ± 42.8 | 85.7 ± 40.5* |
| | 3.0 | 93.3 ± 28.9 | 148.2 ± 32.4 |

*$p < 0.05$ (t-test against control)
n.s. - not significant

It is evident from the above results for the new formation of glucose and glycogen that compounds I and II still do not have any significant effect at 0.3 mg/kg whereas prednicarbate is already exhibiting a small but significant ($p<0.05$, t test) effect at this concentration. A similar situation pertains in relation to the 3 mg/kg dosages, where prednicarbate has a significantly stronger effect than do compounds I and II. The therapeutic advantage (low systemic effect) is therefore greater in the case of the compounds I and II than it is in the case of prednicarbate.

Furthermore, the compounds prednisolone 17-n-butylcarboxylic ester 21-phenyl acetate and betamethasone 17-n-valerate 21-phenyl acetate, for example, also exhibit similar effect profiles to those of compounds I and II.

EXAMPLES

The following general comments should be made with regard to the examples given below:

The melting points are measured in a Tottoli apparatus (from Büchi) or on a type 7841 Kofler hot bench from Reichert (Austria), and are not corrected. The IR spectra (in KBr) are plotted using a Perkin-Elmer 521 grating spectrophotometer. Only the characteristic bands are cited in each case. The UV spectra were plotted (in methanol) using a Beckmann DK 1 A spectrophotometer. The mass spectroscopic investigations (MS) are mainly carried out using an MS 9 apparatus (from AEI). The MS spectra (molecular weight peak) are chiefly given in: MS=m/z= . . . (M+H$^+$) (measurement using pure isotopes), i.e. the monoisotopic molar mass was registered in each case. FAB-MS spectra were measured as a rule. Silica gel $F_{254}$ ready-to-use plates (from Merck) were employed for the thin layer chromatography (TLC). Unless otherwise indicated, methylene chloride:methanol=19:1 was used as the eluent (elution distance 7 cm). Development was carried out twice in each case. The spots were either detected at 254 nm using a UV lamp or else rendered visible either by spraying with 10% methanolic sulfuric acid or by heating at 100° C. The $R_F$ values are in every case only relative. 15 silica gel 60, particle size 0.063–0.2 mm (from Merck), was employed for the column chromatography.

When carbonyl chlorides are used in the reactions, absolute dioxane is often advantageously added to the reaction mixture, for example in the case of substituted benzoyl chlorides where the ratio of dioxane/pyridine is about 1:1, and, in order to accelerate the reaction, the reaction mixture is often, particularly in the case of sterically hindered or less reactive carbonyl chlorides or carboxylic anhydrides, heated at about 60° C. (monitoring of the course of the reactions using TLC).

The reaction products can be characterized by thin layer chromatography (TLC); in this context, the reaction products have $R_F$ values of about 0.65–0.75. As a rule, the reaction products are characterized by mass spectra using MS=m/z= . . . (M+H$^+$) (FAB spectra as a rule); the monoisotopic molar mass is registered in each case. The M+H$^+$ values were rounded up in each case. IR, $^1$H-NMR and UV spectra can also be enlisted for the characterization.

Example 1

Prednisolone 17-n-butyrate 21-[furan-2-carboxylic] ester

A solution of 200 mg of furan-2-carbonyl chloride in 1 ml of absolute dioxane is added dropwise, at 0° C. and while stirring, to a solution of 226 mg of prednisolone 17-butyrate in 2 ml of absolute pyridine. After stirring at 0° C. for 5 to 6 hours (TLC indicates completed formation of the desired reaction product), the mixture is poured into 100 ml of a half-saturated aqueous solution of sodium chloride, and the precipitate (oily or wax) is isolated by way of a fluted filter and taken up with methylene chloride (or ethyl acetate); this mixture is then washed with water and dried with sodium sulfate, and the solvent is distilled off in vacuo. Crystallization then takes place using diisopropyl ether or diethyl ether or petroleum ether, followed by filtering and recrystallization (where appropriate) from ethanol/ether (optionally with the addition of petroleum ether). 160 mg of the abovementioned title compound are obtained with a m.p.: 206° C.

MS: m/z=525 (M+H$^+$)

TLC: $R_F \cong 0.7$

Example 2

Prednisolone 17-n-butyrate 21-(thiophene-2-carboxylic) ester

In a similar manner to that described under Example 1, 230 mg of prednisolone 17-n-butyrate are reacted with 230 mg of thiophene-2-carbonyl chloride instead of the furan-2-carbonyl chloride, and worked up; the title compound is obtained in pure crystalline form. 130 mg of the abovementioned title compound are obtained with a m.p.: 120 to 124° C.

MS: m/z=541 (M+H$^+$)

TLC: $R_F \cong 0.7$

Example 3

Prednisolone 17-n-butyrate 21-(4-methoxybenzoate) (=21-p-anisic ester)

In a similar manner to that described under Example 1, 230 mg of prednisolone 17-n-butyrate are reacted with 240 mg of 4-methoxybenzoyl chloride (=p-anisoyl chloride) instead of the furan-2-carbonyl chloride, and worked up; the title compound is obtained in pure crystalline form. 140 mg of the abovementioned title compound are obtained with a m.p.: 190–192° C.

MS: m/z=565 (M+H$^+$)

TLC: $R_F \cong 0.7$

Example 4

If m-anisoyl chloride or o-anisoyl chloride is employed in accordance with Example 3, prednisolone 17-n-butyrate 21-(3-methoxybenzoate) or prednisolone 17-n-butyrate 21-(2-methoxybenzoate) is then correspondingly obtained. Both reaction products demonstrate MS: m/z=565 (M+H$^+$)

TLC: $R_F \cong 0.7$

Example 5

Prednisolone 17-n-butyrate 21-(3,4-methylenedioxybenzoate)

In a similar manner to that described under Example 1, 230 mg of prednisolone 17-n-butyrate are reacted with 270 mg of 3,4-methylenedioxybenzoyl chloride instead of the furan-2-carbonyl chloride, and worked up; the title compound is obtained in pure crystalline form. 155 mg of the abovementioned title compound are obtained with a m.p.: 210° C.

MS: m/z=579 (M+H$^+$)

TLC: $R_F \cong 0.75$

Example 6

Prednisolone 17-n-butyrate 21-(3)-phenylpropionate

A solution of 300 mg of 3-phenylpropionyl chloride in 1 ml of absolute dioxane is added dropwise, at 0° C. and while stirring, to a solution of 340 mg of prednisolone 17-n-butyrate in 3 ml of absolute pyridine. After stirring at 0° C. for 5 to 6 hours (TLC indicates completed formation of the desired reaction product), the mixture is poured into 100 ml of a half-saturated aqueous solution of sodium chloride, and the precipitate (oily or wax) is isolated by way of a fluted filter and taken up with methylene chloride (or ethyl acetate); this mixture is washed with water and dried with sodium sulfate, and the solvent is distilled off in vacuo. Recrystallization (where appropriate) takes place from ethanol/ether (with the optional addition of petroleum ether). 400 mg of the abovementioned title compound are obtained with a m.p.: 90 to 93° C. (amorphous) (precipitated from petroleum ether)

MS: m/z=563 (M+H$^+$)

TLC: $R_F \cong 0.7$

Example 7

Prednisolone 17-n-butyrate 21-phenoxyacetate

In the same manner as that described under Example 6, 340 mg of prednisolone 17-n-butyrate are reacted with 300 mg of phenoxyacetyl chloride instead of the 3-phenylpropionyl chloride, and worked up. The title compound is obtained in pure crystalline form. 380 mg of the abovementioned title compound are obtained with a m.p.: 93 to 95° C. (precipitated from petroleum ether; amorphous).

MS: m/z=565 (M+H$^+$)

TLC: $R_F \cong 0.7$

Example 8

Prednisolone 17-n-butyrate 21-cinnamic ester

In the same way as described under Example 6, 350 mg of prednisolone 17-n-butyrate are reacted with 320 mg of cinnamoyl chloride instead of the 3-phenylpropionyl chloride; working up takes place and the product is prepared in pure form by crystallization. 300 mg of the abovementioned title compound are obtained.

m.p.: 112° C. (from petroleum ether, amorphous).

MS: m/z=561 (M+H$^+$)

TLC: R$_F \cong$0.7

Example 9

If 360 mg of p-methoxycinnamoyl chloride are employed in

Example 8 instead of the cinnamoyl chloride, 330 mg of prednisolone 17-n-butyrate 21-p-methoxycinnamic ester are obtained with a m.p. of 120° C. (from petroleum ether, amorphous), after analogous working-up, isolation and purification.

MS: m/z=591 (M+H$^+$)

TLC: R$_F \cong$0.8

Example 10

Prednisolone 17-iso-butyrate 21-(thienyl-2-acetic) ester

In the same way as described in Example 8, 0.3 g of prednisolone 17-iso-butyrate is reacted with 0.3 g of 2-thienylacetyl chloride instead of the acid chloride employed in that example, and this is followed by working up and preparation in pure form following crystallization. 240 mg of the abovementioned title compound are obtained from diethyl ether. (TLC-pure wax)

MS: m/z=555 (M+H$^+$)

TLC: R$_F \cong$0.7

Example 11

Prednisolone 17-n-butyrate 21-(thiophene-2-carboxylic) ester

In the same way as described in Example 8, 0.3 g of prednisolone 17-n-butyrate are reacted with 0.3 g of thiophene-2-carbonyl chloride instead of the acid chloride employed in that example. After stirring at 0° C. for 5 hours, working-up takes place and the product is prepared in pure form following crystallization. 260 mg of the abovementioned title compound are obtained from diethyl ether. m.p.: 120 to 124° C.

MS: m/z=541 (M+H$^+$)

TLC: R$_F \cong$0.7

Example 12

Prednisolone 17-n-butyrate 21-[3-(2-thienyl)acrylic] ester

In the same way as described in Example 8, 0.3 g of prednisolone 17-n-butyrate are reacted with 0.31 g of thienyl acryloyl chloride instead of the acid chloride used in that example; working-up takes place and the product is prepared in pure form following crystallization. 280 mg of the abovementioned title compound are obtained from diethyl ether.

m.p.: 176–179° C.

MS: m/z=567 (M+H$^+$); TLC: R$_F \cong$0.7

Example 13

Prednisolone 17-n-butyrate 21-(furan-2-carboxylic) ester

In the same way as described in Example 8, 0.3 g of prednisolone 17-n-butyrate are reacted with 0.3 g of furan-2-carbonyl chloride instead of the acid chloride used in that example; working-up takes place and the product is prepared in pure form following crystallization. 230 mg of the abovementioned title compound are obtained from diethyl ether.

m.p.: 206° C.

MS: m/z=525 (M+H$^+$)

TLC: R$_F \cong$0.7

Example 14

Prednisolone 17-n-butyrate 21-[3-(2-furylacrylic) ester]

In the same way as described in Example 8, 0.3 g of prednisolone 17-n-butyrate are reacted with 0.31 g of β- or 3-(2-furylacryloyl) chloride instead of the acid chloride used in that example; working up takes place and the product is prepared in pure form following crystallization. 250 mg of the abovementioned title compound are obtained from diethyl ether. m.p.: 220–224° C.

MS: m/z=551 (M+H$^+$)

TLC: R$_F \cong$0.7

Example 15

Prednisolone 17-propionate 21-cinnamic ester

In the same way as described under Example 8, 350 mg of prednisolone 17-propionate are reacted with 320 mg of cinnamoyl chloride, and worked up, and the title compound is prepared in pure form. 280 mg of the abovementioned title compound are obtained; m.p.: 105 to 110° C. (from petroleum ether, amorph.).

MS: m/z=547 (M+H$^+$)

TLC: R$_F \cong$0.7

Example 16

Prednisolone 17-n-valerate 21-cinnamic ester

In the same way as described under Example 8, 350 mg of prednisolone 17-n-valerate are reacted with 320 mg of cinnamoyl chloride, and worked up, and the title compound is prepared in pure form. 245 mg of the abovementioned title compound are obtained.

m.p.: 90 to 98° C. (precipitated from petroleum ether).

MS: m/z=575 (M+H$^+$)

TLC: R$_F \cong$0.75

Example 17

Prednisolone 17-propionate 21-(furan-2-carboxylic) ester

In the same way as described in Example 13, 0.3 g of prednisolone 17-propionate are reacted with 0.3 g of furan-2-carboxylic, and worked up, and the title compound is prepared in pure form. 280 mg of the abovementioned title compound, of amorphous consistency, are obtained by precipitation with petroleum ether.

MS: m/z=511

TLC: $R_F \cong 0.7$

Example 18 a) If 0.3 g of 6α-methylprednisolone 17-propionate is employed in the reaction instead of the prednisolone 17-propionate in Example 17, 0.25 g of the analogous 6α-methylprednisolone 17-propionate 21-(furan-2-carboxylic) ester, which was not recrystallized, is then obtained, in amorphous form, following precipitation with petroleum ether.

MS: m/z=525 (M+H$^+$)

TLC: $R_F \cong 0.75$ b) If 0.33 g of 6α-methylprednisolone 17-propionate, instead of the prednisolone-17-n-valerate, is reacted with 0.33 g of cinnamoyl chloride in Example 16, 210 mg of 6α-methylprednisolone 17-propionate 21-cinnamic ester with a m.p.: 125° C. (precipitation with petroleum ether) are then obtained following the same conduct of reaction, working-up and purification.

MS: m/z=561 (M+H$^+$)

TLC: $R_F \cong 0.7$

In an analogous reaction mixture, which is three times as large, 880 mg of reaction product are obtained with a m.p.: 125° C. [Ms: m/z=561 (M+H$^+$)].

Example 19

Prednisolone 17-propionate 21-p-methoxycinnamic ester

In the same way as described in Example 8, 340 mg of prednisolone 17-propionate are reacted with 350 mg of p-methoxycinnamoyl chloride, and worked up and prepared in pure form. 330 mg of the abovementioned title compound are obtained as a wax from petroleum ether.

MS: m/z=577 (M+H$^+$)

TLC: $R_F \cong 0.8$

Example 20

Prednisolone 17-n-butyrate 21-phenylacetate a) In the same way as described under Example 6, 350 mg of prednisolone 17-n-butyrate are reacted with 320 mg of phenylacetyl chloride instead of the 3-phenylpropionyl chloride; working-up takes place and the product is prepared by crystallization. 140 mg of the abovementioned title compound are obtained. m.p.: about 160° C.

MS: m/z=549 (M+H$^+$)

TLC: $R_F \cong 0.8$ (still some subsidiary spots of low intensity present in the TLC above and below the main spot at $R_F \cong 0.8$)

b) A freshly prepared mixture of 30 mg of concentrated sulfuric acid in 2.5 ml of absolute pyridine (suspension of pyridinium sulfate) is added, at 20° C. and while stirring, to a solution of 1.1 g (0.0025 mol) of prednisolone 17-n-butyrate and 1.2 g (0.0088 mol) of phenylacetic acid (dried at about 50 to 60° C. for 5 hours in vacuo over P$_2$O$_5$) in 6 ml of absolute pyridine. After stirring for 15 minutes, 720 mg (0.0035 mol) of N,N'-dicyclohexylcarbodiimide are added. A crystalline precipitate of the N,N'-dicyclohexylurea which has been formed soon separates out from the initially clear solution. The mixture is stirred until starting material can no longer be detected by TLC and the reaction product is detectable at $R_F=0.8$ (as a rule, a reaction time of 16 hours; a longer reaction time, e.g. standing or stirring over the weekend, does not impair the reaction result). After this, 0.3 ml of acetic acid or acetic anhydride is added and the mixture is left to stand for a further 1 hour at 20° C. and then 24 to 48 hours in a deep-freeze (about −15° C.). The precipitated N,N'-dicyclohexylurea is filtered off and washed with cold pyridine (about −15° C.), and the filtrate is stirred into about 400 ml of a quarter-saturated aqueous solution of sodium chloride; about 5 ml of ethanol are added and the oily-crystalline precipitate is filtered off, washed several times with water and then taken up in about 20 ml of methylene chloride. After drying with sodium sulfate, the solvent is distilled off and the residue is crystallized by adding diethyl ether or diisopropyl ether. 1.1 g of prednisolone 17-n-butyrate 21-phenyl acetate with a melting point of about 106° C. are obtained and can be recrystallized from tert-butanol/diethyl ether.

m.p.: 164 to 166° C.

MS: m/z=549 (M+H$^+$)

TLC: $R_F \cong 0.80$ ($R_F$ of SM$\cong$0.45) no subsidiary spots visible above and below $R_F \cong 0.8$.

c) A further mixture is made up which is analogous to that described under Example 20b); however, the acid catalyst, concentrated sulfuric acid in pyridine, is omitted. A TLC sample fails to indicate any further starting material after a reaction period which is about 5 times longer than that given under Example 20b). After working-up and purification which are analogous to those described under Example 20b), 1.0 g of prednisolone 17-n-butyrate 21-phenylacetate is obtained having the same parameters as those given under Example 20b).

The title compound, likewise having the same parameters, is obtained if absolute dimethylformamide is used as the solvent instead of pyridine.

d) A further mixture is prepared which is analogous to that described under Example 20b). However, 60 mg of p-toluenesulfonic acid are added instead of the sulfuric acid. After working-up and purification which are analogous to those given under Example 20b), 1.3 g of prednisolone 17-n-butyrate 21-phenylacetate are obtained having the same parameters as given in Example 20b).

e) 120 mg of 4-dimethylaminopyridine and 1.75 g of dicyclohexylcarbodiimide are added, at 0° C. and while stirring, to a solution of 2.16 g of prednisolone 17-n-butyrate and 1.22 g of phenylacetic acid in 40 ml of absolute methylene chloride. The initially clear reaction solution soon becomes turbid. After stirring at room temperature for about 36 hours, a TLC sample no longer detects any starting material. The mixture is then kept at −15° C. (deep-freeze) for 2 days and the precipitated dicyclohexylurea is filtered off; the latter is washed with methylene chloride cooled to about −15° C. and the organic solvent is then stripped off in vacuo. The remaining residue is crystallized from boiling diethyl ether and recrystallized from ethanol/diethyl ether. 1.9 g of the abovementioned title compound (brilliantly white crystals) are obtained having the same parameters (MS, TLC and melting point) as given under Example 20b). The melting point is about 2° higher than that of Example 2b): m.p.: 166 to 168° C.

f) In an analogous mixture to e), the methylene chloride is replaced as solvent by dimethylformamide. Otherwise, the procedure is exactly as given under Example 20e). After the working-up, 1.7 g of the abovementioned title compound are obtained with a m.p.: 165 to 167° C.

Example 21

Prednisolone 17-propionate 21-phenylacetate

If, as described in Example 20b), 1.1 g of prednisolone 17-propionate are reacted with 1.2 g of phenylacetic acid and 720 mg of N,N'-dicyclohexylcarbodiimide, as well as pyridinium sulfate, in a total of 8.5 ml of absolute pyridine, followed by working-up and preparation of the title compound in pure form, 1.1 g of the abovementioned title compound are then obtained with a m.p.: 168° C (crystallized from diethyl ether).

MS: m/z=535 (M+H$^+$)

TLC: $R_F \cong 0.7$ (almost 0.75)

Example 22

Prednisolone 17-n-valerate 21-phenylacetate

If, in the same way as described in Example 20b), 1.1 g of prednisolone 17-n-valerate are reacted with 1.2 g of phenylacetic acid and 720 mg of N,N'-dicyclohexylcarbodiimide, as well as pyridinium sulfate, in 9 ml of absolute pyridine, and this is followed by working-up and preparation in pure form, 0.8 g of the abovementioned title compound is then obtained (after chromatography) with a m.p.: 178° C. (from diethyl ether).

MS: m/z=563 (M+H$^+$)

TLC: $R_F \cong 0.75$

Example 23

Prednisolone 17-benzoate 21-phenylacetate

If, as described in Example 20b), 1.1 g of prednisolone 17-benzoate are reacted with 1.2 g of phenylacetic acid and 720 mg of N,N'-dicyclohexylcarbodiimide, as well as pyridinium sulfate, in 8 ml of absolute pyridine, and this is followed by working up and preparation in pure form, 850 mg of the abovementioned title compound are then obtained, after crystallization with diisopropyl ether, with a m.p.: 106° C.

MS: m/z=583 (M+H$^+$)

TLC: $R_F \cong 0.8$.

Example 24

Prednisolone 17,21-bis-[phenylacetate]

If, as described in Example 20b), 1.1 g of prednisolone 17-phenyl acetate are reacted with 1.2 g of phenylacetic acid and 730 mg of N,N'-dicyclohexylcarbodiimide, as well as pyridinium sulfate, in 7.5 ml of absolute pyridine, followed by working up and preparation in pure form, 1.0 g of amorphous product, representing the abovementioned title compound, is then obtained following digestion with petroleum ether.

MS: m/z=597 (M+H$^+$)

TLC: $R_F \cong 0.8$

Example 25

6α-Methylprednisolone 17-propionate 21-phenylacetate

If, as described in Example 20b), 2 g of 6α-methylprednisolone 17-propionate are reacted (20° C. for 24 hours) with 1.95 g of phenylacetic acid and 1.3 g of N,N'-dicyclohexylcarbodiimide, as well as pyridinium sulfate (in this case: 60 mg of conc. sulfuric acid+2 ml of absolute pyridine), in 12 ml of abs. pyridine, 1.9 g of the abovementioned title compound are then obtained, after analogous working-up and preparation in pure form (in this case, however, without chromatography) and after grinding with petroleum ether, with a m.p.: 113 to 116° C.

MS: m/z=549 (M+H$^+$)

TLC: $R_F \cong 0.5$

Example 26

Prednisolone 17-propionate 21-(2-thienyl)acetate

If, as described in Example 20b), 1.65 g of prednisolone 17-propionate are reacted with 1.9 g of 2-thienylacetic acid, instead of phenylacetic acid, and 1.1 g of N,N'-dicyclohexylcarbodiimide, as well as pyridinium sulfate (35 g of $H_2SO_4$+2 ml of pyridine), in 8 ml of absolute pyridine, followed by working up and purification in pure form, 800 mg of the abovementioned title compound are then obtained, after chromatography and crystallization from diethyl ether. M.p.: 154 to 158° C.

MS: m/z=541 (M+H$^+$)

TLC: $R_F \cong 0.7$

Example 27

Betamethasone 17-n-valerate 21-phenoxyacetate

A solution of 0.3 ml of phenoxyacetyl chloride in 1 ml of absolute dioxane is added dropwise, at 0° C. and while stirring, to a solution of 300 mg of betamethasone 17-n-valerate in 2 ml of absolute pyridine. After stirring at 0° C. for 5 hours (TLC indicates completed formation of the desired reaction product), the mixture is poured into 50 ml of a half-saturated aqueous solution of sodium chloride. After this mixture has stood at 20° C. for 16 hours, the oily to waxy precipitate is filtered using a fluted filter, washed with water and taken up with methylene chloride (or ethyl acetate); this latter mixture is then washed with water and dried with sodium sulfate, and the solvent is then distilled off in vacuo and the residue digested with petroleum ether. After filtering off, 340 mg of the abovementioned title compound are obtained with a m.p. of 130 to 132° C. The reaction product can be recrystallized from ethanol/diethyl ether, optionally with the addition of petroleum ether.

MS: m/z=611 (M+H$^+$)

TLC: $R_F \cong 0.8$

Example 28

Betamethasone 17-n-valerate 21-(3)-phenylpropionate

In the same way as described in Example 27, 0.3 g of betamethasone 17-n-valerate is reacted with 300 mg of 2-phenylpropionyl chloride, instead of the phenoxyacetyl chloride, in pyridine/dioxane at 0° C. Following analogous working-up and isolation, 310 mg of the abovementioned title compound are obtained from petroleum ether. M.p.: 186° C.

MS: m/z=609 (M+H$^+$)

TLC: $R_F \cong 0.8$

Example 29

Betamethasone 17-n-valerate 21-cinnamic ester

In the same way as described in Example 27, 0.3 g of betamethasone 17-n-valerate is reacted with 0.3 g of cinnamoyl chloride, instead of the phenoxyacetyl chloride, in pyridine/dioxane at 0° C., followed by working up and purification in pure form. 290 mg of the abovementioned title compound are obtained after triturating with diisopropyl ether.

M.p.: 147° C.

MS: m/z=607 (M+H$^+$)

TLC: R$_F$≅0.8

Example 30

Betamethasone 17-n-valerate 21-(4-methoxycinnamic) ester

If 0.35 g of 4-methoxycinnamoyl chloride is employed in Example 29 instead of cinnamoyl chloride, 310 mg of the abovementioned title compound are then obtained after analogous conduct of the reaction, working-up and preparation in pure form.

MS: m/z=637 (M+H$^+$)

TLC: R$_F$≅0.8

Example 31

Betamethasone 17-n-valerate 21-(furan-2-carboxylic) ester

In the same way as described in Example 27, 0.3 g of betamethasone 17-n-valerate is reacted with 0.3 g of furan-2-carbonyl chloride, instead of the phenoxyacetyl chloride, followed by working up and preparation in pure form. 315 mg of the abovementioned title compound are obtained after digesting with petroleum ether. M.p.: 135 to 140° C.

MS: m/z=571 (M+H$^+$)

TLC: R$_F$≅0.8

Example 32

Dexamethasone 17-n-butyrate 21-cinnamic ester

In the same way as described in Example 27, 0.3 g of dexamethasone 17-n-butyrate is reacted with 0.3 g of cinnamoyl chloride, instead of the phenoxyacetyl chloride, in pyridine/dioxane at 0° C., followed by working up and preparation in pure form. 360 mg of the abovementioned title compound are obtained in amorphous form after triturating with petroleum ether.

MS: m/z=593 (M+H$^+$)

TLC: R$_F$≅0.7

Example 33

Dexamethasone 17-n-butyrate (4-methoxycinnamic) ester

If 0.35 g of 4-methoxycinnamoyl chloride is employed in Example 32 instead of cinnamoyl chloride, 315 mg of the abovementioned title compound (amorphous) are then obtained after analogous conduct of the reaction, working up and preparation in pure form.

MS: m/z=623 (M+H$^+$)

TLC: R$_F$≅0.75

Example 34

Betamethasone 17-n-valerate 21-phenylacetate a) In the same way as described in Example 20b), 2.4 g of betamethasone 17-n-valerate are reacted, at 20° C. for 72 hours, with 2.4 g of phenylacetic acid, pyridinium sulfate (69 mg of conc. sulfuric acid in 2 ml of pyridine) and 1.44 g of N,N'-dicyclohexylcarbodiimide in 12 ml of absolute pyridine, followed by working up and preparation in pure form. 1.6 g of the above title compound are obtained after crystallization of the originally waxy precipitate from diethyl ether. M.p.: 178 to 181° C.

MS: m/z=595 (M+H$^+$)

TLC: R$_F$≅0.75 b) In the same way as described in Example 20e), 12 g of betamethasone 17-valerate in 200 ml of methylene chloride are reacted, at 0° C. for 16 hours, with 6.1 g of phenylacetic acid, 8.75 g of N,N'-dicyclohexylcarbodiimide and 600 mg of 4-dimethylaminopyrimidine, followed by working up and preparation in pure form. 6.2 g of the abovementioned title compound, having the same parameters as given under a), are obtained by crystallization from diethyl ether and two recrystallizations from ethanol/methylene chloride+diethyl ether. M.p. 178–179° C.

If, however, the reaction took place in an analogous manner but at room temperature (22° C.) for 24 hours, 8.2 g of betamethasone 17-n-valerate 11,21-bisphenyl acetate (crystallization from ethanol) were then obtained as the main product. M.p. 121° C.;

MS: m/z=713 (M+H$^+$)

TLC: R$_F$≅0.85–0.90

2.8 g of the abovementioned title compound, having the same parameters as under Example 34a), are obtained from the mother liquor following crystallization from diethyl ether.

Example 35

Betamethasone 17-n-valerate 21-(indole-3-acetic) ester

In the same way as described in Example 20e), 230 mg of betamethasone 17-n-valerate in 5 ml of absolute methylene chloride are reacted, at 0° C. for 3 days, with 250 mg of indolyl-3-acetic acid, 180 mg of N,N'-dicyclohexylcarbodiimide and 14 mg of 4-dimethylaminopyridine, followed by working up and preparation in pure form. 175 mg of the abovementioned title compound are obtained after grinding the residue with petroleum ether. M.p.: 120 to 135° C. (amorphous)

MS: m/z=634 (M+H$^+$)

TLC: R$_F$≅0.7

Example 36

Dexamethasone 17-n-butyrate 21-(indole-3-acetic) ester

In the same way as described in Example 35 and Example 20e), 230 mg of dexamethasone 17-n-butyrate are reacted instead of the betamethasone 17-valerate in Example 35, but at 20° C. for 3 days, followed by working up and isolation. 180 mg of the abovementioned title compound are obtained in amorphous form from petroleum ether.

MS: m/z=620 (M+H$^+$)

TLC: R$_F$≅0.7

Example 37

Prednisolone 17-n-butyrate 21-(indole-3-acetic) ester

Pyridinium sulfate (comprising 56 mg of conc. sulfuric acid in 2.5 ml of absol. pyridine, in accordance with Example 20b)) is added, at 20° C. and while stirring, to a solution of 2.2 g of prednisolone 17-n-butyrate and 3.1 g of 3-indoleacetic acid (dried) in 15 ml of absolute pyridine. After the mixture has been stirred at 20° C. for 30 minutes, 1.55 g of N,N'-dicyclohexylcarbodiimide are added. After the mixture has then been stirred at 20° C. for 48 hours, the mass spectrum gives m/z=588 (M+H$^+$) and no m/z=431 (M+H$^+$) for the starting steroid. After further treatment and working-up in analogy with Example 20b), an oily precipitate, which changes into a wax, is obtained after the mixture has been poured into about 500 ml of a half-saturated solution of sodium chloride. The wax is decanted or filtered off, washed with water, and dried in a desiccator in vacuo over $P_2O_5$. 1.55 g of the title compound are obtained as an amorphous product after grinding with petroleum ether.

MS (of wax or amorphous material): m/z=588 (M+H$^+$)

TLC≅0.7 (major spot=Ms+a few weak subsidiary spots).

In order to prepare the substance in pure form, chromatography takes place on silica gel (column: diameter=5 cm; h=20 cm) using methylene chloride/methanol=99.5:0.5. The resulting eluate fractions which have an $R_F$≅0.7 are combined and freed from the solvents by distillation. The residue is crystallized from diethyl ether. 1.3 g of the title compound are obtained with a m.p.: 144° C., and having the same parameters for MS and TLC as the waxy or amorphous title compound.

Example 38 a) Prednisolone 17-acetate 21-phenylacetate

If, as described in Example 37, 0.5 g of prednisolone 17-acetate is reacted, at room temperature, with 0.6 g of phenylacetic acid, instead of the 3-indolylacetic acid, and 360 mg of N,N'-dicyclohexylcarbodiimide as well as 15 mg of concentrated sulfuric acid in 1.25 ml of pyridine (=pyridinium sulfate) in a total of 4.5 ml of absolute pyridine, followed by working up and isolation as a wax or in amorphous form, and (optionally) preparation in pure form by chromatography, 410 mg of prednisolone 17-acetate 21-phenyl acetate are then obtained with a m.p.: 170 to 175° C. (after digestion with diisopropyl ether)

MS: m/z=521 (M+H$^+$) (crystallized, as a wax or in

TLC: $R_F$≅0.7 amorphous form)

In the same way as described in Example 38a), the following are obtained, starting, (instead of from prednisolone 17-acetate)

b) from hydrocortisone 17-n-butyrate, hydrocortisone 17-n-butyrate 21-phenylacetate (MS: m/z=551 (M+H$^+$); $R_F$≅0.8)

c) from cortisone 17-n-butyrate, cortisone 17-n-butyrate 21-phenylacetate ($R_F$≅0.8)

d) from prednisone 17-n-butyrate, prednisone 17-n-butyrate 21-phenylacetate ($R_F$≅0.7)

e) from 6α-fluoroprednisolone 17-n-butyrate, 6α-fluoroprednisolone 17-n-butyrate 21-phenylacetate ($R_F$≅0.8; MS: m/z=567 (M+H$^+$))

f) from 6α-fluorodexamethasone 17-n-butyrate, 6α-fluorodexamethasone 17-n-butyrate 21-phenylacetate ($R_F$≅0.8; MS: m/z 599 (M+H$^+$))

g) from 6α-fluorobetamethasone 17-n-butyrate, 6α-fluorobetamethasone 17-n-butyrate 21-phenylacetate ($R_F$≅0.75)

h) from 6α,16α-dimethylprednisolone 17-n-butyrate, 6α,16α-dimethylprednisolone17-n-butyrate21-phenylacetate ($R_F$≅0.75)

i) from the 17α-n-butyrate of Reichstein's substance S, the 17α-n-butyrate 21-phenylacetate of Reichstein's substance S ($R_F$≅0.85; MS: m/z=535 (M+H$^+$))

j) from beclomethasone 17α-n-butyrate, beclomethasone 17α-n-butyrate 21-phenylacetate ($R_F$=≅0.8)

k) from 6α-methyl-9α-fluoroprednisolone 17-n-butyrate, 6α-methyl-9α-fluoroprednisolone 17-n-butyrate 21-phenylacetate ($R_F$≅0.85; MS: m/z=581 (M+H$^+$))

l) from betamethasone 17-propylate, betamethasone 17-propylate 21-phenylacetate ($R_F$=≅0.8)

m) from dexamethasone 17-n-butyrate, dexamethasone 17-n-butyrate 21-phenylacetate ($R_F$=≅0.75; MS=m/z=581 (M+H$^+$))

n) from dexamethasone 17-n-valerate, dexamethasone 17-n-valerate 21-phenylacetate ($R_F$≅0.75; MS=m/z=595 (M+H$^+$))

as an oil or wax or in the amorphous form or crystallized.

Example 39

Prednisolone 17-n-butyrate 21-phenylacetate a) 120 mg of 4-dimethylaminopyridine and 1.75 g of dicyclohexylcarbodiimide are added, at 0° C. and while stirring, to a solution of 2.10 g of prednisolone 17-n-butyrate and 1.20 g of phenylacetic acid in 40 ml of absolute methylene chloride. The initially clear reaction solution soon becomes turbid. After the mixture has been stirred at room temperature for about 36 hours, a TLC sample no longer detects any starting material. The mixture is then kept at –15° C. (deep freeze) for 2 days, and the precipitated dicyclohexylurea is filtered off and washed with a little methylene chloride which has been cooled down to –15° C., and the organic solvent is stripped off in vacuo. The remaining residue is crystallized from boiling diethyl ether and recrystallized from ethanol/diethyl ether. 1.8 g of the abovementioned title compound, having the same parameters (MS, TLC and melting point) as given under Example 20b), are obtained. The melting point is about 3° higher than that of Example 20b): m.p.: 167 to 169° C.

b) In an analogous mixture to that of Example 31a), the methylene chloride is replaced as a solvent by dimethylformamide. Otherwise, the procedure is exactly as given under Example 39a). After the working-up, 1.7 g of the abovementioned title compound are obtained with a m.p.: 166° C.

Example 40

Prednisolone 17-n-butyrate 21-phenylacetate a) A mixture of 216 mg of prednisolone 17-n-butyrate or 270 mg of 21-(tert-butyldimethylsiloxy)prednisolone 17-n-butyrate, 136 mg of phenylacetic acid, 210 mg of trifluoroacetic anhydride and 6 mg of anhydrous p-toluenesulfonic acid is boiled under reflux for 7 hours in 40 ml of absolute toluene or benzene. After this, the mixture is poured into a 6% aqueous solution of sodium bicarbonate and this mixture is then stirred vigorously. This is followed by washing with water, drying, stripping off the solvent, and carrying out chromatography on silica gel (see Example 20b)). The product migrating at a TLC $R_F$ value≅0.7 is crystallized from diethyl ether. It is identical in all its parameters to the reaction product given under Example 20.

b) In a further mixture, 1.5 g of phenylacetic acid and 0.75 ml of trifluoroacetic anhydride are added to 700 mg of prednisolone 17-n-butyrate in 20 ml of absolute dioxane. After the mixture has been stirred at 20° C. for 30 hours, 40 ml of water, containing 2 g of sodium bicarbonate, were stirred in. After having been dried, the resultant waxy product is chromatographed as under Example 20b) and crystallized from diethyl ether. The abovementioned title compound, having the same parameters as given under Example 20b), is obtained.

Example 41a

Prednisolone 17-n-butyrate 21-[4-(4-(N,N)-bis(2-chloroethyl)amino)phenyl)butyrate]

Pyridinium sulfate (comprising 110 mg of conc. sulfuric acid in 2.5 ml of abs. pyridine, prepared in accordance with Example 20b)) is added, at 20° C. and while stirring, to a solution of 4.32 g of prednisolone 17-n-butyrate and 3.5 g (4-(4-(N,N-bis(2-chloroethyl)amino)phenyl)butyric acid (=chlorambucil) in 30 ml of absolute pyridine. After the mixture has been stirred at 20° C. for 20 minutes, 3 g of N,N'-dicyclohexylcarbodiimide are added. After this mixture has been stirred at 20° C. for 48 hours, 100 ml of ethyl acetate and 100 ml of water+ice are added to it. The pH is adjusted to ≅2.5 to 3.0 with 5N hydrochloric acid (aqu.), and the organic phase is washed successively with water, sodium carbonate solution (aqu.) and water. After drying ($Na_2SO_4$), the solvent is stripped off in a rotary evaporator and the residue is digested with petroleum ether. The amorphous reaction product is filtered off and dried over $P_2O_5$ in vacuo. 5.0 g of the abovementioned title compound, which exhibits a main spot at $R_F \cong 0.8$ in TLC, are obtained.

Example 41b

Optimization of the Process Originally Given in Example 41 (≅41a)):

Prednisolone 17-n-butyrate 21-[4-(4-(N,N)-(bis(2-chloroethyl)amino)phenyl)butyrate] (crystallized product)

Pyridinium sulfate (comprising 300 mg of conc. sulfuric acid in 10 ml of absol. pyridine, prepared in accordance with Example 20b) is added, at 20° C. and while stirring, to a solution of 8.6 of prednisolone 17-n-butyrate and 7.2 g of 4-(4-(N,N)-(bis(2-chloroethyl)amino)phenyl)-butyric acid (=chlorambucil) in 50 ml of absol. pyridine. After the mixture has been stirred at 20° C. for 20 minutes, 5.77 g of N,N'-dicyclohexylcarbodiimide are added. After the mixture has been stirred at 20° C. for 48 hrs, 2 ml of glacial acetic acid are added and the mixture is left to stand for 48 hrs in a deep freeze (−15° C.). The precipitated N,N'-dicyclohexylurea (6.1 g) is filtered off and approximately 300 ml of a half-saturated, aqueous solution of sodium chloride are added to the filtrate, whereupon an oil precipitates out. The oil is filtered off using a fluted filter and treated with 400 ml of water, as a result of which it changes into a wax within 48 hrs. The wax is filtered off, washed with water and dried, the final occasion being in a vacuum desiccator. It is dissolved under reflux in boiling isopropanol and the mixture is then left to cool to 20° C., whereupon a thick crystalline crop soon precipitates out. The latter is filtered off and washed with isopropanol cooled to 0° C. After drying, 7.0 g of the abovementioned title compound are obtained in crystalline form. Mp. from 112 to 115° C.

MS: m/z=716

TLC: $R_F \cong 0.8$

Example 42

Prednisolone 17-n-butyrate 21-phenylacetate 435 mg of N,N'-dicyclohexylcarbodiimide, 43 mg of N,N-dimethylaminopyridine and 700 mg of prednisolone 17-n-butyrate were added in succession, at 0° C. and while stirring, to a solution of 286 mg of phenylacetic acid in 14 ml of absolute methylene chloride. After this mixture had been stirred at 20° C. for 18 hours, it is washed with 40 ml of a saturated aqueous solution of sodium hydrogen carbonate, with 30 ml of aqueous hydrochloric acid (2 mol $dm^{-3}$) and water. The methylene chloride phase is evaporated off on a rotary evaporator in vacuo and the residue is crystallized from ethanol/methylene chloride/diethyl ether. 570 mg of the abovementioned title compound, which is identical in all its parameters with the product obtained in accordance with Examples 20 a) or 20b), are obtained.

Example 43

Prednisolone 17-n-butyrate 21-phenylacetate 150 mg of phenylacetic acid and 430 mg of prednisolone 17-n-butyrate are dissolved in 3 ml of abs. methylene chloride and 5 ml of absolute pyridine, and 0.25 ml of a 50% solution of propylphosphonic anhydride in absolute methylene chloride, and 10 mg of 4-dimethylaminopyridine, are then added to this solution. After the mixture has been stirred at about 40° C. (oil bath) for 8 hours, it is poured into ice water which contains sodium bicarbonate for neutralization. Extraction with ethyl acetate then takes place, followed by washing with an aqueous solution of $KHSO_4$ and with water. After distilling off solvent, the residue is chromatographed on silica gel. In addition to starting material and prednisolone, an eluate fraction also contains the desired abovementioned title compound, which has the same parameters as given under Example 20b).

Example 44

Prednisolone 17-n-butyrate 21-phenylacetate

A solution of 400 ml of phenylacetic anhydride in 1 ml of absolute dioxane is added dropwise, at 0° C. and while stirring, to a solution of 220 mg of prednisolone 17-n-butyrate in 2 ml of absolute pyridine. After this mixture has been stirred at 0C for 5 to 6 hours and at 20° C. for 16 hours, it is poured into 100 ml of a half-saturated aqueous solution of sodium chloride, and the waxy precipitate is isolated using a fluted filter and taken up with methylene chloride (or ethyl acetate); this latter solution is washed with water and dried with sodium sulfate, after which the solvent is distilled off in vacuo. Crystallization then takes place with diisopropyl ether or diethyl ether or petroleum ether, and this is followed by filtration and recrystallization from ethanol/ether (optionally with the addition of petroleum ether). 135 mg of the abovementioned title compound are obtained with a m.p.: 165° C.

MS: m/z=549 (M+H$^+$)

TLC: $R_F \cong 0.7$

Example 45

Prednisolone 17-n-butyrate 21-[3, 4-methylenedioxybenzoic] ester

In the same way as described under Example 44, 220 mg of prednisolone 17-n-butyrate are reacted with 280 mg of 3,4-(methylenedioxy)benzoyl chloride or 600 mg of 3,4-(methylenedioxy)benzoic anhydride, instead of the phenylacetic anhydride, after which working up takes place. 160 mg of the abovementioned title compound are obtained as a wax (from petroleum ether).

MS: m/z=579 (M+H$^+$)

TLC: $R_F \cong 0.7$

Example 46

Prednisolone 17-n-butyrate 21-phenylcarbonate

A solution of 4 ml of phenyl chloroformate in 12 ml of absolute dioxane is added dropwise, at 0° C. and while stirring, to a solution of 2.20 g of prednisolone 17-n-butyrate in 9 ml of absolute pyridine, whereupon an oily precipitate appeared. After this mixture has been stirred at 0° C. for 7 hours, it is poured into 200 ml of a half-saturated solution (aqu.) of sodium chloride, and the precipitated oil is filtered off using a fluted filter and taken up with methylene chloride, and the residue is chromatographed on silica gel (35 to 70 my) using methylene chloride/methanol=99.5:0.5. The fractions of $R_F \cong 0.75$ are combined and crystallized from diisopropyl ether. 1.1 g of the abovementioned title compound are obtained with a m.p.: 119° C. (indefinite).
MS: m/z=551 (M+H$^+$)
TLC: $R_F \cong 0.7$

Example 47

Prednisolone 17-n-butyrate 21-(9-fluorenylmethyl) carbonate

In the same way as described under Example 46, 2.20 g of prednisolone 17-n-butyrate are reacted with 7.5 g of 9-fluorenylmethyl chloroformate, and this is followed by working up and preparation of the product. 1.4 g of the abovementioned title compound are obtained as an amorphous product (from petroleum ether).

MS: m/z=653 (M+H$^+$)
TLC: $R_F \cong 0.7$

Example 48

Prednisolone 17-n-butyrate 21-phenylacetate a) A solution of 500 mg of prednisolone 17-n-butyrate 21-mesylate (or an equimolar quantity of the analogous 21-p-chlorobenzenesulfonate), 145 mg of phenylacetic acid and 112 mg of triethylamine (under these circumstances, intermediate formation of the triethylammoniumphenylacetate takes place) in 25 ml of dimethylformamide (or acetonitrile) is stirred at about 45° C. (oil bath) for 3 hours. After this, the dimethylformamide, or acetonitrile, is distilled off in vacuo and the residue is treated with 30 ml of methylene chloride. The organic phase is washed in succession with 1N aqueous hydrochloric acid and then 4 times with water. After chromatography in accordance with Example 46, and crystallization from diethyl ether, the abovementioned title compound is obtained, having the same parameters as given under Example 20b).

b) The same title compound can be obtained if 600 mg of prednisolone 17-n-butyrate 21-desoxy 21-iodide, 150 mg of phenylacetic acid and 2.5 ml of triethylamine are boiled under reflux for 45 minutes in 25 ml of acetonitrile, and working up and isolation are then carried out as described under a).

c) 600 mg of prednisolone 17-n-butyrate 21-desoxy 21-iodide are heated together with 200 ml of potassium phenyl acetate (Rhone-Poulenc) at 100° C. (oil bath), while stirring, in 25 ml of absolute dimethylformamide for 40 minutes. After that, the mixture is cooled down and poured into a half-saturated aqueous solution of sodium chloride, whereupon an oily wax, which can be filtered off, precipitates out, which wax, after having been filtered off, washed with water and dried (vacuum over $P_2O_5$) is chromatographed on silica gel in accordance with Example 46 and, after crystallization, yields the abovementioned title compound having the same parameters as in Examples 20a) and 20b).

Example 49

6α-Methylprednisolone 17-n-butyrate 21-cinnamic ester

In the same way as described in Example 27, 0.3 g of 6α-methyl 17-n-butyrate, instead of the betamethasone 17-n-valerate, is reacted with 350 mg of cinnamoyl chloride, instead of the phenoxyacetyl chloride, in pyridine/dioxane at 0° C. Following analogous working-up and isolation, the abovementioned title compound is obtained in amorphous form by precipitating with N-hexane and can be crystallized from ethanol/diethyl ether.

MS:=575 (M+H$^+$)
TLC: $R_F \cong 0.8$

Example 50

Prednisone 17-n-butyrate 21-cinnamic ester

In the same way as described in Example 27, 0.3 g of prednisone 17-n-butyrate, instead of the betamethasone 17-n-valerate, is reacted with 350 mg of cinnamoyl chloride, instead of the phenoxyacetyl chloride, in pyridine/dioxane at 0° C. Following analogous working-up and isolation, the abovementioned title compound is obtained in amorphous form by precipitating with petroleum ether.

MS:=559 (M+H$^+$)
TLC: $R_F \cong 0.75$

Example 51

Prednisolone 17-benzoate 21-cinnamic ester

In the same way as described under Example 6, 350 mg of prednisolone 17-benzoate, instead of the prednisolone 17-n-butyrate, are reacted with 320 mg of cinnamoyl chloride in pyridine/dioxane at 0° C. Following analogous working-up and isolation, the abovementioned title compound is obtained in amorphous form by precipitating with petroleum ether.

MS:=595 (M+H$^+$)
TLC: $R_F \cong 0.8$

Example 52

Prednisolone 17-benzoate 21-p-methoxycinnamic ester

If 380 mg of p-methoxycinnamoyl chloride are employed in Example 51 instead of the cinnamoyl chloride, the abovementioned title compound (amorphous) is then obtained, following analogous conduct of the reaction, working-up and isolation, by precipitating with petroleum ether.

MS:=625 (M+H$^+$)
TLC: $R_F \cong 0.8$

Example 53

Betamethasone 17-benzoate 21-cinnamic ester

In the same way as described under Example 6, 360 mg of betamethazone 17-benzoate, instead of the prednisolone 17-n-butyrate, are reacted with 320 mg of cinnamoyl chloride in pyridine/dioxane at 0° C. Following analogous working-up and isolation, the abovementioned title compound (amorphous) is obtained by precipitating with petroleum ether.

MS:=628 (M+H$^+$)

TLC: R$_F$≅0.8

Example 54

Betamethasone 17-benzoate 21-p-methoxycinnamic ester

If 380 mg of p-methoxycinnamoyl chloride are employed in Example 53 instead of the cinnamoyl chloride, the abovementioned title compound is then obtained in amorphous form, following analogous conduct of the reaction, working-up and isolation, by precipitating with petroleum ether.

MS:=658 (M+H$^+$)

TLC: R$_F$≅0.8

Example 55

Prednisolone 17-n-butyrate 21-(4-phenyl)cinnamic ester 84 mg of 4-dimethylamino pyridine and 1.75 g of dicyclohexylcarbodiimide are added, at 0° C. and while stirring, to a solution of 3.0 g of prednisolone 17-n-butyrate and 2.0 g of 4-phenylcinnamic acid in 60 ml of absol. methylene chloride. The reaction solution, which is initially clear, soon becomes turbid. After the mixture has been stirred at room temperature for about 6 hours, a TLC sample indicates that starting material is no longer present. The mixture is then stored at +4° C. for 2 days and at −15° C. (deep freeze) for 2 days, after which the precipitated dicyclohexylurea is filtered off and washed with a little methylene chloride which has been cooled to −15° C.; the organic solvent is then stripped off in vacuo. The residue which remains is crystallized from boiling diethyl ether and recrystallized from ethanol/diethyl ether. 2.2 g of the abovementioned title compound are obtained with a m.p. of 192° C.

MS: m/z=637 (M+H$^+$)

TLC: R$_F$≅0.8

Example 56

Prednisolone 17-n-butyrate 21-(trans-3,4-methylenedioxy)cinnamic ester

In the same way as described in Example 55, 3 g of prednisolone 17-n-butyrate are reacted with 2.1 g of trans-3,4-methylenedioxycinnamic acid, instead of 4-phenylcinnamic acid, and the product is worked up, isolated and prepared in pure form. 2.0 g of the abovementioned title compound are obtained.

MS: m/z=605 (M+H$^+$)

TLC: R$_F$≅0.8

Example 57

Prednisolone 17-n-butyrate 21-phenylpropionic ester

In the same way as described in Example 55, 3 g of prednisolone 17-n-butyrate are reacted (reaction time, 24 hrs) with 1.9 g of phenylpropionic acid, instead of 4-phenylcinnamic acid, followed by working-up and isolation. After several weeks, the abovementioned title compound crystallizes slowly, in crystalline form, out of the resulting oil (2.0 g) and can only be prepared in pure form with difficulty. Gauging of the oily/crystalline crude product.

MS: m/z=559 (M+H$^+$)

TLC: R$_F$≅0.8

Example 58

Prednisolone 17-n-butyrate 21-(5-phenylpenta-2,4-dienoic)ester

In the same way as described in Example 55, 3 g of prednisolone 17-n-butyrate are reacted with 1.56 g of 5-phenylpenta-2,4-dienoic acid (=cinnamylidineacetic acid), instead of 4-phenylcinnamic acid, followed by working-up, isolation and preparation in pure form. 3.0 g of the abovementioned title compound are obtained with a m.p. of 161° C.

MS: m/z=587 (M+H$^+$)

TLC: R$_F$≅0.8

Example 59

Betamethasone 17-benzoate 21-phenylacetate

Pyridinium sulfate (prepared from 50 mg of conc. sulfuric acid in 1.7 ml of absol. pyridine in accordance with Example 20b)) is added, at 20° C. and while stirring, to a solution of 1.37 g of betamethasone 17-benzoate and 1.32 g of phenylacetic acid (dried) in 6 ml of absol. pyridine. After the mixture has been stirred (20° C.) for 30 minutes, 790 mg of N,N'-dicyclohexylcarbodiimide are added. After the mixture has been stirred at 20° C. for 60 hrs, TLC indicates complete conversion to the abovementioned title compound. Following the addition of 0.25 ml of acetic anhydride, the mixture is stored in a deep freeze (−15° C.) for 24 hours. The precipitated dicyclohexylurea is filtered off and then washed with 10 ml of absol. pyridine (−15° C.); the filtrate is then concentrated on a high vacuum pump. 1.75 g are obtained of a wax which is chromatographed on silica gel (Merck AG, 35–70 my) (column packing: 24 cm in height, 3.5 cm in width) using approximately 1 l of acid-free methylene chloride+0.5% added methanol. After distilling of the eluent, 820 mg of the abovementioned title compound are obtained, following grinding and crystallization using diisopropyl ether, in a form which is highly pure by TLC.

M.p. 186° C.

MS:=616; (M+H$^+$)

TLC: R$_F$=0.85

Example 60

Betamethasone 17-benzoate 21-(indole-3-acetic) ester

If an analogous reaction to that described under Example 59 is carried out using 170 g of 3-indolylacetic acid, instead of the phenylacetic acid, 930 mg of the abovementioned title compound are then obtained, following analogous conduct of reaction, working-up, isolation and chromatography, after grinding with diisopropyl ether.

M.p. 145–149° C. (amorphous?)

MS:=655 (M+H$^+$)

TLC: R$_F$≅0.8

Example 61

Prednisolone 17-benzoate 21-(indole-3-acetic) ester

If 1.30 g of prednisolone 17-benzoate are employed in Example 60 instead of betamethasone 17-benzoate, 780 mg of the abovementioned title compound (amorphous) are then obtained, following analogous conduct of the reaction, working-up, isolation and chromatography, after grinding with diisopropyl ether.

MS:=623 (M+H$^+$)

TLC: R$_F$≅0.8

The examples in Tables 1 and 2 below, where R(1)' is the entire side chain on the 21CH$_2$—O group, are analogous to the above examples.

It was only the molecular weight peaks (m/z= . . . (M+H$^+$), obtained from the mass spectra, which were in each case evaluated (as oil or wax or in amorphous form or crystallized) for characterizing the synthesis products, and this was not, as a rule, followed by any purification by crystallization (recrystallization) or chromatography.

TABLE 1

Basic corticoid: prednisolone

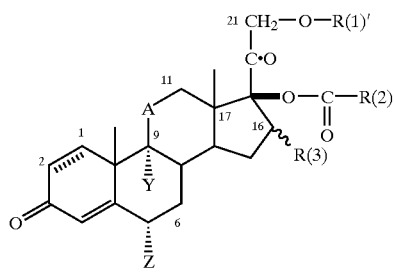

I

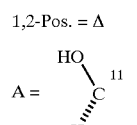

1,2-Pos. = Δ

R(3) = H
Y = H
Z = H
Δ = 1,2 double bond

| Run No. | Carboxylic acid, carbonyl chloride or carboxylic anhydride employed | Process variant according to Example | R(2) | R(1)' | MS (m/z) (M + H$^+$) |
|---|---|---|---|---|---|
| 1.1 | Cl—C$_6$H$_4$—COCl | 6 | —C$_3$H$_7$ | Cl—C$_6$H$_4$—CO— | 541 |
| 1.2 | CH$_3$CONH—C$_6$H$_4$—COCl | 6 | —C$_3$H$_7$ | CH$_3$CONH—C$_6$H$_4$—CO— | 592 |
| 1.3 | CH$_3$S—C$_6$H$_4$—CO$_2$H | 20b, e | —C$_3$H$_7$ | CH$_3$S—C$_6$H$_4$—CO— | 581 |
| 1.4 | C$_6$H$_5$—SCH$_2$CO$_2$H | 20b, e | —C$_3$H$_7$ | C$_6$H$_5$—SCH$_2$CO— | 581 |
| 1.5 | C$_6$H$_5$—(CH$_2$)$_3$CO$_2$H | 20b, e | —C$_3$H$_7$ | C$_6$H$_5$—(CH$_2$)$_3$CO— | 577 |
| 1.6 | HO$_2$C-pyridine-CO$_2$H | 20b, e (2 equ, corticoid) | —C$_3$H$_7$ | pyridine-CO— —OC (dimer) | 993 |
| 1.7 | CH$_3$—C$_6$H$_4$—COCl (p-CH$_3$, m, o) | 6 | —C$_3$H$_7$ | CH$_3$—C$_6$H$_4$—CO— (p, m, o) | 549 |
| 1.8 | m-CH$_3$—C$_6$H$_4$—CO$_2$H | 20b, e | n-C$_4$H$_9$ | m-H$_3$C—C$_6$H$_4$—CO— | 563 |

TABLE 1-continued

Basic corticoid: prednisolone

I 1,2-Pos. = Δ

A = (HO, C-11, H)

R(3) = H
Y = H
Z = H
Δ = 1,2 double bond

| Run No. | Carboxylic acid, carbonyl chloride or carboxylic anhydride employed | Process variant according to Example | R(2) | R(1)' | MS (m/z) (M + H$^+$) |
|---|---|---|---|---|---|
| 1.9 | pyridin-3-yl-CH$_2$CO$_2$H | 20b, e | —C$_3$H$_7$ | pyridin-3-yl-CH$_2$CO— | 550 |
| 1.10 | pyridin-3-yl-CH=CH—CO$_2$H | 20b, e | —C$_3$H$_7$ | pyridin-3-yl-CH=CH—CO— | 562 |

Note:
—C$_3$H$_7$ in the tables in each case denotes n-C$_3$—H$_7$ (n-butyrate)

TABLE 2

Basic corticoid: prednisolone

I 1,2-Pos. = Δ

A = (HO, C-11, H)

R(3) = H
Y = H
Z = H
Δ = 1,2 double bond

| Run No. | Carboxylic acid, carbonyl chloride or carboxylic anhydride employed | Process variant according to Example | R(2) | R(1)' | MS (m/z) (M + H$^+$) |
|---|---|---|---|---|---|
| 2.1 | thiophen-3-yl-COCl | 6 | —C$_3$H$_7$ | thiophen-3-yl-CO— | 541 |
| 2.2 | thiophen-3-yl-CH$_2$CO$_2$H | 20b, e | —C$_3$H$_7$ | thiophen-3-yl-CH$_2$CO— | 555 |
| 2.3 | thiophen-2-yl-CH$_2$CH$_2$COCl | 6 | —C$_3$H$_7$ | thiophen-2-yl-CH$_2$CH$_2$CO— | 569 |

TABLE 2-continued

Basic corticoid: prednisolone

R(3) = H
Y = H
Z = H
Δ = 1,2 double bond

| Run No. | Carboxylic acid, carbonyl chloride or carboxylic anhydride employed | Process variant according to Example | R(2) | R(1)' | MS (m/z) (M + H$^+$) |
|---|---|---|---|---|---|
| 2.4 | 5-chloro-thiophene-2-COCl | 6 | —C$_3$H$_7$ | 5-chloro-thiophene-2-CO— | 576.5 |
| 2.5 | furan-3-CO$_2$H | 20b, e | —C$_3$H$_7$ | furan-3-CO— | 525 |
| 2.6 | pyridine-2,6-di-CO$_2$H | 20b, e | n-C$_4$H$_9$ | furan-3-CO— | 539 |
| 2.7 | furan-3-CO$_2$H | 20b, e | n-C$_5$H$_{11}$ | furan-3-CO— | 553 |
| 2.8 | furan-2-CH$_2$CH$_2$COCl | 6 | —C$_3$H$_7$ | furan-2-CH$_2$CH$_2$CO— | 553 |
| 2.9 | 5-methyl-furan-2-CO$_2$H | 20b, e | —C$_3$H$_7$ | 5-methyl-furan-2-CO— | 539 |
| 2.10 | pyrrole-2-CO$_2$H | 20b, e | —C$_3$H$_7$ | pyrrole-2-CO— | 524 |
| 2.11 | thiazole-4-CO$_2$H | 20b, e | —C$_3$H$_7$ | thiazole-4-CO— | 542 |
| 2.12 | furan-2-CH$_2$OCOCl | 6.46 | —C$_3$H$_7$ | furan-2-CH$_2$OCO— | 555 |
| 2.13 | indole-3-CO$_2$H | 20b, e | —C$_3$H$_7$ | indole-3-CO— | 574 |

TABLE 2-continued

Basic corticoid: prednisolone

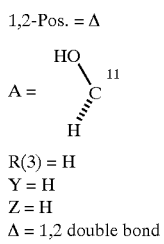

R(3) = H
Y = H
Z = H
Δ = 1,2 double bond

| Run No. | Carboxylic acid, carbonyl chloride or carboxylic anhydride employed | Process variant according to Example | R(2) | R(1)' | MS (m/z) (M + H⁺) |
|---|---|---|---|---|---|
| 2.14 | indol-3-yl-CH₂—CO₂H (2-methyl) | 20b, e | —C₃H₇ | indol-3-yl-CH₂—CO— (2-methyl) | 602 |
| 2.15 | N-methylindol-2-yl—CO₂H | 20b, e | —C₃H₇ | N-methylindol-2-yl—CO— | 588 |
| 2.16 | 4-benzoylbenzoic acid | 20b, e | —C₃H₇ | 4-benzoylbenzoyl— | 639 |
| 2.17 | 5-methoxyindol-3-yl-CH₂—CO₂H | 20b, e | —C₃H₇ | 5-methoxyindol-3-yl-CH₂—CO— | 618 |
| 2.18 | naphth-2-yl-CH₂—CO₂H | 20b, e | —C₃H₇ | naphth-2-yl-CH₂—CO— | 599 |
| 2.19 | quinoxalin-2-yl—CO—Cl | 6 | —C₃H₇ | quinoxalin-2-yl—CO— | 587 |
| 2.20 | isoquinolin-1-yl—CO₂H | 20b, e | —C₃H₇ | isoquinolin-1-yl—CO— | 586 |
| 2.21 | indol-3-yl-CH=CH—CO₂H | 20b, e | —C₃H₇ | indol-3-yl-CH=CH—CO— | 600 |

TABLE 2-continued

Basic corticoid: prednisolone

R(3) = H
Y = H
Z = H
Δ = 1,2 double bond

| Run No. | Carboxylic acid, carbonyl chloride or carboxylic anhydride employed | Process variant according to Example | R(2) | R(1)' | MS (m/z) (M + H⁺) |
|---|---|---|---|---|---|
| 2.22 | 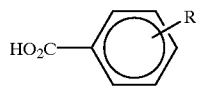 | 20b, e | —C₃H₇ | 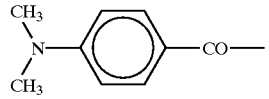 | 578 |

Note:
R(2) in the table is in each case n-C₃—H₇ (n-butyrate)

List 2

A) The following carboxylic acids of the formula IV, or their activated derivatives, are examples of suitable starting compounds:

1. Monosubstituted or polysubstituted benzoic acids of the formula

HO₂C—⟨benzene⟩—R

R=substituted (once or more than once) alkoxy, methylenedioxy, acylamino, dialkylamino, fluorine, chlorine, mercaptoalkyl, phenoxy, alkyl, dialkylamino or amino:

2-, 3- or 4-methoxybenzoic acid; 2-, 3- or 4-chlorobenzoic acid; fluorobenzoic acid; 2,4-, 3,4- or 2,6-difluoro- or dichlorobenzoic acid; 2-, 3- or 4-methylbenzoic acid; 3,5-dimethylbenzoic acid; 3- or 4-trifluorobenzoic acid; 4-acetaminobenzoic acid, 4-acetaminomethylbenzoic acid, 4-(t-butoxy)benzoic acid; 4-t-butylbenzoic acid; 3,4-methylenedioxybenzoic acid; 2,3-, 3,5- or 2,6-dimethoxybenzoic acid; 2,3,4-trimethoxybenzoic acid; 4-BOC-aminobenzoic acid; 4-mercaptomethylbenzoic acid; 4-phenoxybenzoic acid; 4-aminobenzoic acid (PABA) and 4-(dimethylamino)benzoic acid;

2. Heteroaromatic carboxylic acids substituted pyridinecarboxylic acids, preferably 2-mercaptomethylnicotinic acid; 2-chloronicotinic acid, 2-fluoronicotinic acid; methoxynicotinic acid; 6-chloronicotinic acid; 6-acetamidonicotinic acid; pyrazine-2-carboxylic acid; 6,6'-dithiodinicotinic acid; 2-methylnicotinic acid; thiophene-2- or -3-carboxylic acid; 5- or 4-methylthiophene-2 or -3-carboxylic acid; 5- or 4-chlorothiophene-2- or -3-carboxylic acid; furan-2- or -3-carboxylic acid; 5-chloro- and 5-methyl-furan-2-carboxylic acids; 5-nitrofuran-2-carboxylic acid, furan-2,5-dicarboxylic acid;

Pyrrole-2-carboxylic acid; imidazole-2-carboxylic acid; 3-isopropoxythiophene-5-carboxylic acid and 5-chlorothiophene-2-carboxylic acid;

3. Arylacetic and hetarylacetic acids and analogs and/or homologs
a.) Non-fused acids Phenylacetic acid; 2-methyl- or 3-methyl- or 4-methylphenylacetic acid, 4-tert-butylphenylacetic acid; 2-chloro- or 3-chloro- or 4-chlorophenylacetic acid; 2,6-dichloro- or 3,4-dichlorophenylacetic acid; 2-fluoro- or 3-fluoro- or 4-fluorophenylacetic acid; 2,6-difluorophenylacetic acid; 2-nitro- or 3-nitro- or 4-nitrophenylacetic acid; 2,4-dinitrophenylacetic acid; 2-methoxy- or 3-methoxy- or 4-methoxyphenylacetic acid; 4-benzyloxyphenylacetic acid; 3-chloro-4-methoxyphenylacetic acid; 3-bromo-4-methoxyphenylacetic acid; 3-nitro-4-methoxyphenylacetic acid; 3,4-dimethoxyphenylacetic acid; 2,3,4-trimethoxyphenylacetic acid; 3,4-methylenedioxyphenylacetic acid; 3,4-diethoxyphenylacetic acid; 4-biphenylacetic acid; 3-phenoxyphenylacetic acid; 2-acetamino- or 3-acetamino- or 4-acetaminophenylacetic acid; 3-(N)-BOC-aminophenylacetic acid; 4-formylaminophenylacetic acid; 4-N,N-dimethylaminophenylacetic acid;

4-Benzyloxyphenylacetic acid; 4-(2-methoxybenzyloxy) phenylacetic acid; 4-(4-fluorobenzyloxy)phenylacetic acids; 2-(thiazol-4-yl)acetic acid; 2-(thiazol-4-yl)-2-methoxyiminoacetic acid; 3-phenylpropionic acid; D,L-2-phenylpropionic acid; 3-[4-methylphenyl] propionic acid, 3-[4-chloro- or 4-fluoro- or 4-methoxyphenyl] propionic acids; (S)-(+)-2-phenylpropionic acid; (R)-(−)-2-phenylpropionic acid; 4-phenylbutyric acid; phenoxyacetic acid and derivatives (substituents in the phenyl moiety); cis- or (preferred) trans-cinnamic acid; 2-, 3- or 4-methoxycinnamic acid; 4-ethoxycinnamic acid; 3,4-dimethoxycinnamic acid; 3,4,5-trimethoxycinnamic acid; 4-fluorocinnamic acid; 3- or 4-chlorocinnamic acid; 3-bromocinnamic acid; 2- or 3-nitrocinnamic acid; 4-cyanocinnamic acid; 4-isopropylcinnamic acid; 4-tert-butylcinnamic acid, 2- or 4-trifluoromethylcinnamic acid; D,L- or (S)- or (R)-2-(4-isobutylphenyl)propionic acid (Ibuprofen); 4-(isobutylphenyl)-acetic acid (Ibufenac); phenylmercaptoacetic acid; phenylpropiolic acid; 2-methyl-3-(4-tetradecyloxyphenyl)-2-propenoic acid (MTPA); 3-(4-crotyloxyphenyl)propionic acid; 4-dodecylbenzoylacetic acid (DBAA); benzoylacrylic acid; chlorambucil; 3,4,5-trimethoxybenzoylacrylic acid; 2-(4-(thiazol-2-yl)phenyl) propionic acid; 2-(xanthonoxy)acetic acid; 2-phenylcyclopropanecarboxylic acids (trans); 3-(phenylmercapto)acrylic acid; (4-phenyl)butyric acid;

2-thienylacetic acid; 3-thienylacetic acid; N-methylpyrrole-2-carboxylic acid; furylacetic acid; 2-, 3- or 4-pyridylacetic acid;

3-(2-Furyl)acrylic acid; 3-(2-thienyl)acrylic acid; 3-(3-thienyl)acrylic acid; 3-(4- or 2-pyridyl)acrylic acid; 3-(2-thienyl)propionic acids; 3-(2-furyl)-propionic acid; 3-(4-imidazolyl)acrylic acid; (N-methylpyrrol-2-yl)acetic acid;

b.) Fused acids

Indole-2-carboxylic acid; indole-3-carboxylic acid; indole-4-carboxylic acid; (N-methyl)indole-2-carboxylic acid; 2- or 1-naphthalenecarboxylic acid; 2- or 3- or 4-quinolinecarboxylic acid; xanthene-α-carboxylic acid; 1-fluorenecarboxylic acid; 9-fluorenone-4-carboxylic acid;

3-Indolylacetic acid; 2-indolylacetic acid; (N-methyl)-2- or -3-indolylacetic acid; 3-(3-indolyl)-propionic acid; 3- or 2-indolylacrylic acid (also (N-methyl)); (2-methyl-3-indolyl)acetic acid, 3,4-(methylenedioxy)phenylacetic acid; 3,4-(methylenedioxy)cinnamic acid; indole-3-butyric acid; (5-methoxyindol-3-yl)acetic acid; naphthyl-1- or -2-acetic acid; pyrazine-2-carboxylic acid; flavone-8-acetic acid; 5,6-dimethylxanthone-4-acetic acid (L. L. Thomsen et al.: Cancer Chemother, Pharmacol. 31, 151ff. (1992) demonstrate that the corticoid 21-carboxylic esters prepared from this could also have an antitumorigenic effect).

B) The following chloroformic esters (haloformates) of the formula III are examples of suitable starting compounds:

Phenyl chloroformate
Benzyl chloroformate
4-Bromophenyl chloroformate
α-Chloro-2-fluorobenzyl chloroformate
4-Chlorophenyl chloroformate
(+) or (−)-1-(9-fluorenyl)ethyl chloroformate
9-Fluorenylmethyl chloroformate
4-Fluorophenyl chloroformate
4-Methoxyphenyl chloroformate
2-Nitrophenyl chloroformate
p-Tolyl chloroformate Mono- or bis-chloroformic esters of 1.): 2,5-bis-(hydroxymethyl) furan and of 2.): 2,6-bis-(hydroxymethyl)-pyridine Chloroformic esters of 2-hydroxymethylfuran.

What is claimed is:

1. A corticoid 17,21-dicarboxylic ester or corticosteroid 17-carboxylic ester 21-carbonic ester of the formula I:

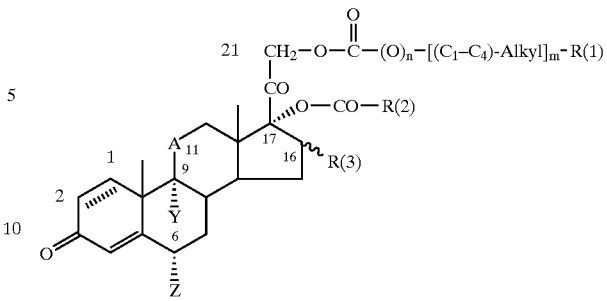

wherein:
A is CHOH or CHCl in arbitrary steric arrangement, $CH_2$, C=O or 9(11) double bond,
Y is hydrogen, fluorine or chlorine,
Z is hydrogen, fluorine or methyl,
R(1) is unsubstituted phenyl or phenyl substituted by one to three substituents selected from the group consisting of methoxy, chlorine, fluorine, methyl, trifluoromethyl, acetamino, acetaminomethyl, t-butoxy, t-butyl, 3,4-methylenedioxy, BOC-amino, amino and dimethylamino,
$(C_1–C_4)$-alkyl is saturated,
n is zero,
m is 1,
R(2) is linear or branched $(C_1–C_8)$-alkyl,

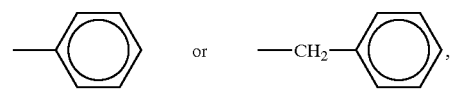

R(3) is hydrogen or α- or β-methyl.

2. A compound as claimed in claim 1, wherein R(2) is

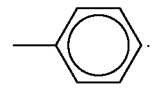

3. A compound as claimed in claim 1, wherein A is CHOH, Y is hydrogen, Z is hydrogen, $(C_1–C_4)$-alkyl is $C_1$-alkyl, R(1) is unsubstituted phenyl, R(2) is

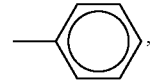

and R(3) is hydrogen.

4. A compound as claimed in claim 1, wherein A is CHOH, Y is fluorine, Z is hydrogen, $(C_1–C_4)$-alkyl is $C_1$-alkyl, R(1) is unsubstituted phenyl, R(2) is

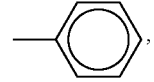

and R(3) is β-methyl.

5. A pharmaceutical composition, which comprises an effective amount of at least one compound as claimed in claim 1, together with a pharmaceutically acceptable additive.

6. A method for treating dermatoses, which comprises applying to skin in need of the treatment an effective amount of at least one compound as claimed in claim 1.

7. A method as claimed in claim 6, wherein the dermatoses are inflammatory and allergic.

8. A process for preparing a compound as claimed in claim 1, which comprises reacting a) a compound of the formula II:

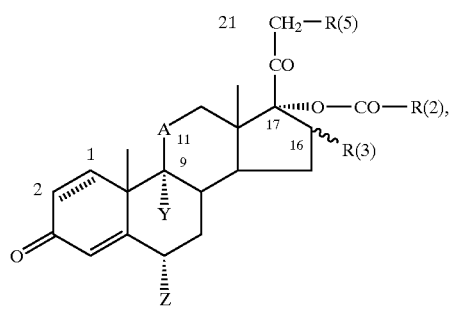

in which R(5) is OH and the remaining substituents are as defined in claim 1, a1) with an activated carboxylic acid of the formula III:

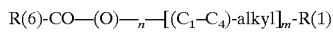

in which:
n is zero,
m is 1, and
(C1–C4)-alkyl and R(1) are as defined in claim 11, and
R(6) is Cl, Br, O[—CO—(O)$_n$—[(C$_1$–C$_4$-alkyl]$_m$-R(1)]$_1^-$, —O—C(O)—CF$_3$, or another activated acid radical, or a3) with a carboxylic acid of the formula III itself, in which
R(6) is OH, and
n is zero,
and the other substituents are given in formula III, in the presence of a water-eliminating reagent, or which comprises reacting b) a compound of the formula II:

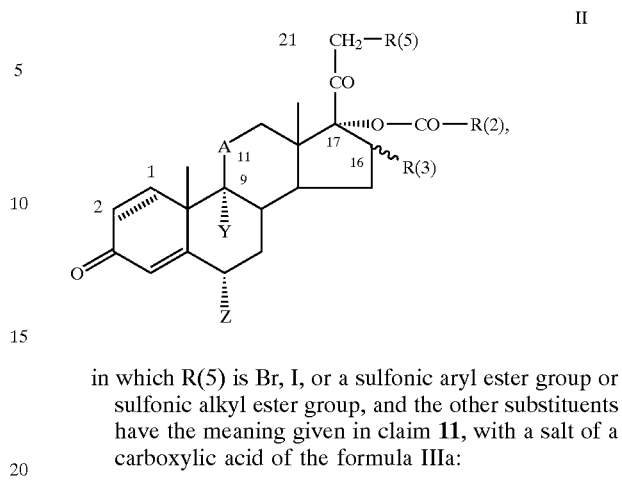

in which R(5) is Br, I, or a sulfonic aryl ester group or sulfonic alkyl ester group, and the other substituents have the meaning given in claim 11, with a salt of a carboxylic acid of the formula IIIa:

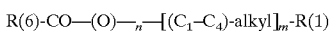

in which
R(6) is —[O$^-$Me$^+$], and
n is zero,
and the other substituents have the meanings given in formula III.

9. A process as claimed in claim 8, wherein in a1) the activated carboxylic acid of formula III is a halide or anhydride or azolide.

10. A process as claimed in claim 8, wherein in a3) the water eliminating reagent is DCCI.

11. A process as claimed in claim 8, wherein in b) the salt of the carboxylic acid of the formula III is a potassium, sodium, or trialkylammonium salt.

12. A process as claimed in claim 8, wherein in b) Me or R(6) is the cation of an alkali metal salt or of a trialkylammonium salt.

* * * * *

UNITED STATES PATENT AND TRADEMARK OFFICE
CERTIFICATE OF CORRECTION

PATENT NO. : 6,835,724 B2  
DATED : December 28, 2004  
INVENTOR(S) : Ulrich Stache et al.

Page 1 of 2

It is certified that error appears in the above-identified patent and that said Letters Patent is hereby corrected as shown below:

Title page,  
Item [57], ABSTRACT,  
Line 7,

"
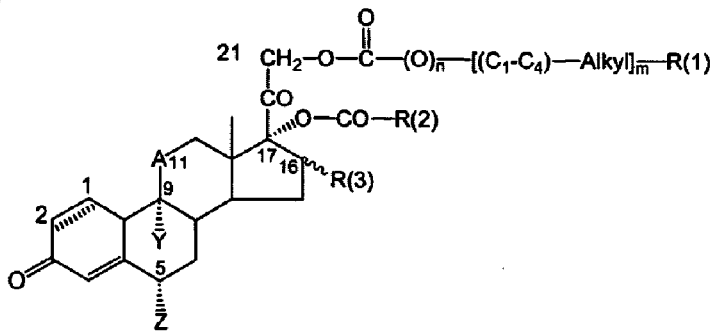
"

should read

--
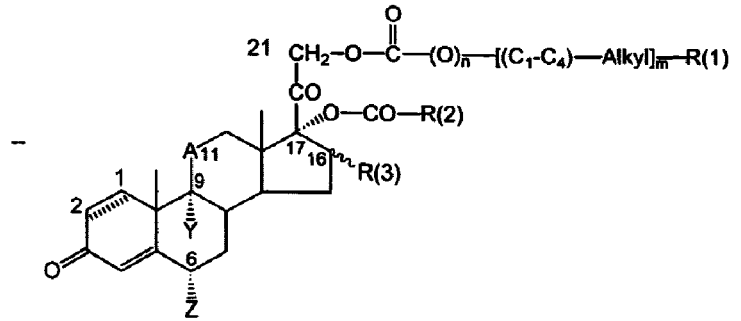
--.

Column 41,  
Line 25, "R(6)-CO-(O)-$_n$-[(C$_1$-C$_4$)-alkyl$_m$-R(1)" should read  
-- R(6)-CO-(O)$_n$-[(C$_1$-C$_4$)-alkyl]$_m$-R(1) --  
Line 30, "(C1-C4)-alkyl" should read -- (C$_1$-C$_4$)-alkyl --.  
Line 30, "claim 11," should read -- claim 1, --.

Column 42,  
Line 19, "claim 11," should read -- claim 1, --.  
Line 20, "formula IIIa," should read -- formula III --.

UNITED STATES PATENT AND TRADEMARK OFFICE
CERTIFICATE OF CORRECTION

PATENT NO. : 6,835,724 B2
DATED : December 28, 2004
INVENTOR(S) : Ulrich Stache et al.

It is certified that error appears in the above-identified patent and that said Letters Patent is hereby corrected as shown below:

Column 42 (cont'd),
Line 22, "$R(6)\text{-}CO\text{-}(O)\text{-}_n\text{-}[(C_1\text{-}C_4)\text{-}alkyl]_m\text{-}R(1)$ (III)" should read
-- $R(6)\text{-}CO\text{-}(O)_n\text{-}[(C_1\text{-}C_4)\text{-}alkyl]_m\text{-}R(1)$ (III) --.

Signed and Sealed this

Thirty-first Day of May, 2005

JON W. DUDAS
*Director of the United States Patent and Trademark Office*